(12) United States Patent
Clayton et al.

(10) Patent No.: US 7,953,471 B2
(45) Date of Patent: *May 31, 2011

(54) METHOD AND APPARATUS FOR IMPLANTATION BETWEEN TWO VERTEBRAL BODIES

(75) Inventors: John B. Clayton, Superior, CO (US); Y. Raja Rempersaud, Toronto (CA)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/509,868

(22) Filed: Jul. 27, 2009

(65) Prior Publication Data

US 2009/0299477 A1 Dec. 3, 2009

Related U.S. Application Data

(63) Continuation of application No. 10/837,997, filed on May 3, 2004, now Pat. No. 7,567,834.

(51) Int. Cl.
*A61B 5/05* (2006.01)
(52) U.S. Cl. ........... 600/424; 600/427
(58) Field of Classification Search .......... 600/407, 600/424, 427; 128/920
See application file for complete search history.

(56) References Cited

U.S. PATENT DOCUMENTS

| | | |
|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |

(Continued)

FOREIGN PATENT DOCUMENTS

CA 964149 A1 3/1975

(Continued)

OTHER PUBLICATIONS

"Prestige Cervical Disc System Surgical Technique", 12 pgs.

(Continued)

*Primary Examiner* — Long V Le
*Assistant Examiner* — Michael T Rozanski
(74) *Attorney, Agent, or Firm* — Harness, Dickey

(57) ABSTRACT

A method and system to assist in a planning and navigation of procedure. Generally, the system allows for image acquisition of a selected area of the anatomy. The images may then be used to mark various points to determine true anatomical definitions and planes. The definitions may assist in positioning a prosthesis.

33 Claims, 10 Drawing Sheets

U.S. PATENT DOCUMENTS

| | | |
|---|---|---|
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |

| Patent | Date | Inventor |
|---|---|---|
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |

| Patent | Date | Name |
|---|---|---|
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,295 A | 10/1997 | Ray et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,697,377 A | 12/1997 | Wittkampf |
| 5,702,406 A | 12/1997 | Vilsmeier et al. |
| 5,711,299 A | 1/1998 | Manwaring et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,669 A | 6/1998 | Hansen et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,823,192 A | 10/1998 | Kalend et al. |
| 5,823,958 A | 10/1998 | Truppe |
| 5,824,093 A | 10/1998 | Ray et al. |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,938,603 A | 8/1999 | Ponzi |
| 5,938,694 A | 8/1999 | Jaraczewski et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,956,796 A | 9/1999 | Lodato |
| 5,957,844 A | 9/1999 | Dekel et al. |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,096,050 A | 8/2000 | Audette |
| 6,104,944 A | 8/2000 | Martinelli |
| 6,118,845 A | 9/2000 | Simon et al. |
| 6,122,538 A | 9/2000 | Sliwa, Jr. et al. |
| 6,122,541 A | 9/2000 | Cosman et al. |
| 6,127,597 A | 10/2000 | Beyar et al. |
| 6,131,396 A | 10/2000 | Duerr et al. |
| 6,132,465 A | 10/2000 | Ray et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 | 1/2001 | Ferre et al. |

| | | |
|---|---|---|
| 6,178,345 B1 | 1/2001 | Vilsmeier et al. |
| 6,194,639 B1 | 2/2001 | Botella et al. |
| 6,201,387 B1 | 3/2001 | Govari |
| 6,203,196 B1 | 3/2001 | Meyer et al. |
| 6,203,497 B1 | 3/2001 | Dekel et al. |
| 6,203,543 B1 | 3/2001 | Glossop |
| 6,211,666 B1 | 4/2001 | Acker |
| 6,223,067 B1 | 4/2001 | Vilsmeier et al. |
| 6,226,548 B1 | 5/2001 | Foley et al. |
| 6,233,476 B1 | 5/2001 | Strommer et al. |
| 6,246,231 B1 | 6/2001 | Ashe |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,306,177 B1 | 10/2001 | Felt et al. |
| 6,314,310 B1 | 11/2001 | Ben-Haim et al. |
| 6,332,089 B1 | 12/2001 | Acker et al. |
| 6,341,231 B1 | 1/2002 | Ferre et al. |
| 6,351,659 B1 | 2/2002 | Vilsmeier |
| 6,370,224 B1 | 4/2002 | Simon et al. |
| 6,381,485 B1 | 4/2002 | Hunter et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,445,943 B1 | 9/2002 | Ferre et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,490,475 B1 | 12/2002 | Seeley et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,510,198 B2 | 1/2003 | Simon et al. |
| 6,516,046 B1 | 2/2003 | Frohlich et al. |
| 6,527,443 B1 | 3/2003 | Vilsmeier et al. |
| 6,551,325 B2 | 4/2003 | Neubauer et al. |
| 6,582,467 B1 | 6/2003 | Teitelbaum et al. |
| 6,584,174 B2 | 6/2003 | Schubert et al. |
| 6,602,291 B1 | 8/2003 | Ray et al. |
| 6,609,022 B2 | 8/2003 | Vilsmeier et al. |
| 6,611,700 B1 | 8/2003 | Vilsmeier et al. |
| 6,620,196 B1 | 9/2003 | Trieu |
| 6,640,128 B2 | 10/2003 | Vilsmeier et al. |
| 6,694,162 B2 | 2/2004 | Hartlep |
| 6,701,179 B1 | 3/2004 | Martinelli et al. |
| 6,827,723 B2 | 12/2004 | Carson |
| RE39,133 E | 6/2006 | Clayton et al. |
| RE40,852 E | 7/2009 | Martinelli et al. |
| RE41,066 E | 12/2009 | Martinelli et al. |
| 2001/0007918 A1 | 7/2001 | Vilsmeier et al. |
| 2002/0095081 A1 | 7/2002 | Vilsmeier et al. |
| 2002/0156363 A1 | 10/2002 | Hunter et al. |
| 2003/0023311 A1 | 1/2003 | Trieu |
| 2003/0072416 A1 | 4/2003 | Rasche et al. |
| 2003/0199984 A1 | 10/2003 | Trieu |
| 2003/0235266 A1 | 12/2003 | Gregerson et al. |
| 2004/0006341 A1 | 1/2004 | Shaolian et al. |
| 2004/0006344 A1 | 1/2004 | Nguyen et al. |
| 2004/0013225 A1 | 1/2004 | Gregerson et al. |
| 2004/0013239 A1 | 1/2004 | Gregerson et al. |
| 2004/0024309 A1 | 2/2004 | Ferre et al. |
| 2004/0039305 A1 | 2/2004 | Eberhart et al. |
| 2004/0039306 A1 | 2/2004 | Eberhart et al. |
| 2004/0152970 A1 | 8/2004 | Hunter et al. |
| 2004/0152972 A1 | 8/2004 | Hunter |
| 2004/0171924 A1 | 9/2004 | Mire et al. |
| 2004/0181149 A1 | 9/2004 | Langlotz et al. |
| 2004/0215071 A1 | 10/2004 | Frank et al. |
| 2005/0085714 A1 | 4/2005 | Foley et al. |
| 2005/0277832 A1 | 12/2005 | Foley et al. |
| 2009/0234217 A1 | 9/2009 | Mire et al. |
| 2009/0290771 A1 | 11/2009 | Frank et al. |
| 2010/0137707 A1 | 6/2010 | Hunter et al. |

FOREIGN PATENT DOCUMENTS

| | | |
|---|---|---|
| DE | 3042343 A1 | 6/1982 |
| DE | 3508730 | 9/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19715202 A1 | 10/1998 |
| DE | 19751761 A1 | 10/1998 |
| DE | 19832296 | 2/1999 |
| DE | 19747427 A1 | 5/1999 |
| DE | 10085137 T0 | 11/2002 |
| EP | 0062941 | 10/1982 |
| EP | 0119660 A1 | 9/1984 |
| EP | 0155857 | 9/1985 |
| EP | 0319844 | 6/1989 |
| EP | 0326768 A2 | 8/1989 |
| EP | 0350996 A1 | 1/1990 |
| EP | 0419729 A1 | 4/1991 |
| EP | 0427358 | 5/1991 |
| EP | 0456103 | 11/1991 |
| EP | 0581704 A1 | 2/1994 |
| EP | 0651968 A1 | 5/1995 |
| EP | 0655138 A1 | 5/1995 |
| EP | 0894473 A2 | 2/1999 |
| EP | 0908146 A2 | 4/1999 |
| EP | 0930046 A2 | 7/1999 |
| FR | 2417970 A1 | 9/1979 |
| FR | 2618211 | 1/1989 |
| GB | 2094590 A | 9/1982 |
| GB | 2164856 A | 4/1986 |
| JP | 62327 | 6/1985 |
| JP | 63240851 | 10/1988 |
| JP | 2765738 T | 4/1991 |
| JP | 3267054 | 11/1991 |
| JP | 6194639 | 7/1994 |
| WO | WO-8809151 A1 | 12/1988 |
| WO | WO-8905123 | 6/1989 |
| WO | WO-9005494 A1 | 5/1990 |
| WO | WO-9103982 A1 | 4/1991 |
| WO | WO-9104711 A1 | 4/1991 |
| WO | WO-9107726 A1 | 5/1991 |
| WO | WO-9203090 A1 | 3/1992 |
| WO | WO-9206645 A1 | 4/1992 |
| WO | WO-9404938 A1 | 3/1994 |
| WO | WO-9423647 A1 | 10/1994 |
| WO | WO-9424933 A1 | 11/1994 |
| WO | WO-9507055 A1 | 3/1995 |
| WO | WO-9611624 | 4/1996 |
| WO | WO-9632059 A1 | 10/1996 |
| WO | WO-9736192 A1 | 10/1997 |
| WO | WO-9749453 A1 | 12/1997 |
| WO | WO-9808554 A1 | 3/1998 |
| WO | WO-9838908 A1 | 9/1998 |
| WO | WO-9915097 A2 | 4/1999 |
| WO | WO-9921498 A1 | 5/1999 |
| WO | WO-9923956 A1 | 5/1999 |
| WO | WO-9926549 A1 | 6/1999 |
| WO | WO-9927839 A2 | 6/1999 |
| WO | WO-9929253 A1 | 6/1999 |
| WO | WO-9933406 A1 | 7/1999 |
| WO | WO-9937208 A1 | 7/1999 |
| WO | WO-9938449 A1 | 8/1999 |
| WO | WO-9952094 A1 | 10/1999 |
| WO | WO-9960939 A1 | 12/1999 |
| WO | WO-0064367 A1 | 11/2000 |
| WO | WO-0130437 A1 | 5/2001 |
| WO | WO-2004070573 A2 | 8/2004 |

OTHER PUBLICATIONS

Adams et al., "Orientation Aid for Head and Neck Surgeons," Innov. Tech. Biol. Med., vol. 13, No. 4, 1992, pp. 409-424.

Adams et al., Computer-Assisted Surgery, IEEE Computer Graphics & Applications, pp. 43-51, (May 1990).

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 6, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Benzel et al., "Magnetic Source Imaging: a Review of the Magnes System of Biomagnetic Technologies Incorporated," Neurosurgery, vol. 33, No. 2 (Aug. 1993), pp. 252-259.

Bergstrom et al. Stereotaxic Computed Tomography, Am. J. Roentgenol, vol. 127 pp. 167-170 (1976).

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR '98, pp. 716-722.

Brown, R., M.D., A Stereotactic Head Frame for Use with CT Body Scanners, Investigative Radiology .COPYRGT. J.B. Lippincott Company, pp. 300-304 (Jul.-Aug. 1979).

Bryan, "Bryan Cervical Disc System Single Level Surgical Technique", Spinal Dynamics, 2002, pp. 1-33.

Bucholz et al., "Variables affecting the accuracy of stereotactic localizationusing computerized tomography," Journal of Neurosurgery, vol. 79, Nov. 1993, pp. 667-673.

Bucholz, R.D., et al. Image-guided surgical techniques for infections and trauma of the central nervous system, Neurosurg. Clinics of N.A., vol. 7, No. 2, pp. 187-200 (1996).

Bucholz, R.D., et al., A Comparison of Sonic Digitizers Versus Light Emitting Diode-Based Localization; Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).

Bucholz, R.D., et al., Intraoperative Ultrasonic Brain Shift Monitor and Analysis, Stealth Station Marketing Brochure (2 pages) (undated).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics andComputer-Assisted Surgery, Grenoble, France, pp. 459-466 (Mar. 19-22, 1997).

Champleboux et al., "Accurate Calibration of Cameras and Range Imaging Sensors: the NPBS Method," IEEE International Conference on Robotics and Automation, Nice, France, May 1992.

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," IEEE Engineering in Medicine and Biology, May/Jun. 1995, pp. 254-263.

Cinquin et al., "Computer Assisted Medical Interventions," International Advanced Robotics Programme, Sep. 1989, pp. 63-65.

Clarysse et al., "A Computer-Assisted System for 3-D Frameless Localization in Stereotaxic MRI," IEEE Transactions on Medical Imaging, vol. 10, No. 4, Dec. 1991, pp. 523-529.

Cutting M.D. et al., Optical Tracking of Bone Fragments During Craniofacial Surgery, Second Annual International Symposium on Medical Robotics and Computer Assisted Surgery, pp. 221-225, (Nov. 1995).

European Search Report mailed Feb. 6, 2006 for EP05103683 claiming benefit of U.S. Appl. No. 10/837,997, filed May 3, 2004.

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Foley et al., "Image-guided Intraoperative Spinal Localization," Intraoperative Neuroprotection, Chapter 19, 1996, pp. 325-340.

Foley, "The StealthStation: Three-Dimensional Image-Interactive Guidance for the Spine Surgeon," Spinal Frontiers, Apr. 1996, pp. 7-9.

Friets, E.M., et al, A Frameless Stereotaxic Operating Microscope for Neurosurgery, IEEE Trans. on Biomed. Eng., vol. 36, No. 6, pp. 608-617 (Jul. 1989).

Gallen, C.C., et al., Intracranial Neurosurgery Guided by Functional Imaging, Surg. Neurol., vol. 42, pp. 523-530 (1994).

Galloway, R.L. et al., Interactive Image-Guided Neurosurgery, IEEE Trans. on Biomed. Eng., vol. 89, No. 12, pp. 1226-1231 (1992).

Galloway, R.L., Jr. et al, Optical localization for interactive, image-guided neurosurgery, SPIE, vol. 2164, pp. 137-145 (undated.

Germano, "Instrumentation, Technique and Technology", Neurosurgery, vol. 37, No. 2, Aug. 1995, pp. 348-350.

Gildenberg et al., "Calculation of Stereotactic Coordinates from the Computed Tomographic Scan," Neurosurgery, vol. 10, No. 5, May 1982, pp. 580-586.

Gomez, C.R., et al., Transcranial Doppler Ultrasound Following Closed Head Injury: Vasospasm or Vasoparalysis?, Surg. Neurol., vol. 35, pp. 30-35 (1991).

Gonzalez, "Digital Image Fundamentals," Digital Image Processing, Second Edition, 1987, pp. 52-54.

Gottesfeld Brown et al., "Registration of Planar Film Radiographs with Computer Tomography," Proceedings of MMBIA, Jun. 1996, pp. 42-51.

Grimson, W.E.L., An Automatic Registration Method for Frameless Stereotaxy, Image Guided Surgery, and enhanced Reality Visualization, IEEE, pp. 430-436 (1994).

Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6,pp. 62-69 (Jun. 1999).

Gueziec et al., "Registration of Computed Tomography Data to a Surgical Robot Using Fluoroscopy: A Feasibility Study," Computer Science/Mathematics, Sep. 27, 1996, 6 pages.

Guthrie, B.L., Graphic-Interactive Cranial Surgery: The Operating Arm System, Handbook of Stereotaxy Using the CRW Apparatus, Chapter 13, pp. 193-211 (undated.

Hamadeh et al, "Kinematic Study of Lumbar Spine Using Functional Radiographies and 3D/2D Registration," TIMC UMR 5525—IMAG.

Hamadeh et al., "Automated 3-Dimensional Computed Tomographic and Fluorscopic Image Registration," Computer Aided Surgery (1998), 3:11-19.

Hamadeh et al., "Towards Automatic Registration Between CT and X-ray Images: Cooperation Between 3D/2D Registration and 2D Edge Detection," MRCAS '95, pp. 39-46.

Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).

Hatch, "Reference-Display System for the Integration of CT Scanning and the Operating Microscope," Thesis, Thayer School of Engineering, Oct. 1984, pp. 1-189.

Hatch, et al., "Reference-Display System for the Integration of CT Scanning and the Operating Microscope", Proceedings of the Eleventh Annual Northeast Bioengineering Conference, Mar. 14-15, 1985, pp. 252-254.

Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).

Heilbrun, M.P., Computed Tomography—Guided Stereotactic Systems, Clinical Neurosurgery, Chapter 31, pp. 564-581 (1983).

Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).

Heilburn et al., "Preliminary experience with Brown-Roberts-Wells (BRW) computerized tomography stereotaxic guidance system," Journal of Neurosurgery, vol. 59, Aug. 1983, pp. 217-222.

Henderson et al., "An Accurate and Ergonomic Method of Registration for Image-guided Neurosurgery," Computerized Medical Imaging and Graphics, vol. 18, No. 4, Jul.-Aug. 1994, pp. 273-277.

Hoerenz, "The Operating Microscope I. Optical Principles, Illumination Systems, and Support Systems," Journal of Microsurgery, vol. 1, 1980, pp. 364-369.

Hofstetter et al., "Fluoroscopy Based Surgical Navigation—Concept and Clinical Applications," Computer Assisted Radiology and Surgery, 1997, pp. 956-960.

Horner et al., "A Comparison of CT-Stereotaxic Brain Biopsy Techniques," Investigative Radiology, Sep.-Oct. 1984, pp. 367-373.

Hounsfield, "Computerized transverse axial scanning (tomography): Part 1. Description of system," British Journal of Radiology, vol. 46, No. 552, Dec. 1973, pp. 1016-1022.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

Jacques et al., "Computerized three-dimensional stereotaxic removal of small central nervous system lesion in patients," J. Neurosurg., vol. 53, Dec. 1980, pp. 816-820.

Joskowicz et al., "Computer-Aided Image-Guided Bone Fracture Surgery: Concept and Implementation," CAR '98, pp. 710-715.

Kall, B., The Impact of Computer and Imgaging Technology on Stereotactic Surgery, Proceedings of the Meeting of the American Society for Stereotactic and Functional Neurosurgery, pp. 10-22 (1987).

Kato, A., et al., A frameless, armless navigational system for computer-assisted neurosurgery, J. Neurosurg., vol. 74, pp. 845-849 (May 1991).

Kelly et al., "Computer-assisted stereotaxic laser resection of intra-axial brain neoplasms," Journal of Neurosurgery, vol. 64, Mar. 1986, pp. 427-439.

Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.

Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).

Kelly, P.J., Computer-Directed Stereotactic Resection of Brain Tumors, Neurologica Operative Atlas, vol. 1, No. 4, pp. 299-313 (1991).

Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).

Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).

Kim, W.S. et al., A Helmet Mounted Display for Telerobotics, IEEE, pp. 543-547 (1988).

Klimek, L., et al., Long-Term Experience with Different Types of Localization Systems in Skull-Base Surgery, Ear, Nose & Throat Surgery, Chapter 51, pp. 635-638 (undated).

Kosugi, Y., et al., An Articulated Neurosurgical Navigation System Using MRI and CT Images, IEEE Trans. on Biomed. Eng. vol. 35, No. 2, pp. 147-152 (Feb. 1988).

Krybus, W., et al., Navigation Support for Surgery by Means of Optical Position Detection, Computer Assisted Radiology Proceed. of the Intl. Symp. CAR'91 Computed Assisted Radiology, pp. 362-366 (Jul. 3-6, 1991).

Kwoh, Y.S., Ph.D., et al., A New Computerized Tomographic-Aided Robotic Stereotaxis System, Robotics Age, vol. 7, No. 6, pp. 17-22 (Jun. 1985).

Laitinen et al., "An Adapter for Computed Tomography-Guided, Stereotaxis," Surg. Neurol., 1985, pp. 559-566.

Laitinen, "Noninvasive multipurpose stereoadapter," Neurological Research, Jun. 1987, pp. 137-141.

Lavallee et al, "Matching 3-D Smooth Surfaces with their 2-D Projections using 3-D Distance Maps," SPIE, vol. 1570, Geometric Methods in Computer Vision, 1991, pp. 322-336.

Lavallee et al., "Computer Assisted Driving of a Needle into the Brain," Proceedings of the International Symposium CAR '89, Computer Assisted Radiology, 1989, pp. 416-420.

Lavallee et al., "Computer Assisted Interventionist Imaging: The Instance of Stereotactic Brain Surgery," North-Holland MEDINFO 89, Part 1, 1989, pp. 613-617.

Lavallee et al., "Computer Assisted Spine Surgery: A Technique For Accurate Transpedicular Screw Fixation Using CT Data and a 3-D Optical Localizer," TIMC, Faculte de Medecine de Grenoble.

Lavallee et al., "Image guided operating robot: a clinical application in stereotactic neurosurgery," Proceedings of the 1992 IEEE International Conference on Robotics and Automation, May 1992, pp. 618-624.

Lavallee et al., "Matching of Medical Images for Computed and Robot Assisted Surgery," IEEE EMBS, Orlando, 1991.

Lavallee, "A New System for Computer Assisted Neurosurgery," IEEE Engineering in Medicine & Biology Society 11th Annual International Conference, 1989, pp. 0926-0927.

Lavallee, "VI Adaption de la Methodologie a Quelques Applications Cliniques," Chapitre VI, pp. 133-148.

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).

Lavallee, S., et al., Computer Assisted Medical Interventions, NATO ASI Series, vol. F 60, 3d Imaging in Medic., pp. 301-312 (1990).

Leavitt, D.D., et al., Dynamic Field Shaping to Optimize Stereotactic Radiosurgery, I.J. Rad. Onc. Biol. Physc., vol. 21, pp. 1247-1255 (1991).

Leksell et al., "Stereotaxis and Tomography—A Technical Note," ACTA Neurochirurgica, vol. 52, 1980, pp. 1-7.

Lemieux et al., "A Patient-to-Computed-Tomography Image Registration Method Based on Digitally Reconstructed Radiographs," Med. Phys. 21 (11), Nov. 1994, pp. 1749-1760.

Levin et al., "The Brain: Integrated Three-dimensional Display of MR and PET Images," Radiology, vol. 172, No. 3, Sep. 1989, pp. 783-789.

Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.

Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Merloz, et al., "Computer Assisted Spine Surgery", Clinical Assisted Spine Surgery, No. 337, pp. 86-96.

Ng, W.S. et al., Robotic Surgery—A First-Hand Experience in Transurethral Resection of the Prostate Surgery, IEEE Eng. in Med. and Biology, pp. 120-125 (Mar. 1993).

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Penn, R.D., et al., Stereotactic Surgery with Image Processing of Computerized Tomographic Scans, Neurosurgery, vol. 3, No. 2, pp. 157-163 (Sep.-Oct. 1978).

Phillips et al., "Image Guided Orthopaedic Surgery Design and Analysis," Trans Inst. MC, vol. 17, No. 5, 1995, pp. 251-264.

Pixsys, 3-D Digitizing Accessories, by Pixsys (marketing brochure)(undated) (2 pages).

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989.

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Entfernung tiefliegender Gefa.beta.mi .beta.bildungen mit Hilfe der Sonar-Stereometrie (Microsurgical Removal of Deep-Seated Vascular Malformations Using Sonar Stereometry). Ultraschall in Med. 12, pp. 80-83(1991).

Reinhardt, Hans. F., Neuronavigation: A Ten-Year Review, Neurosurgery, pp. 329-341 (undated).

Roberts et al., "A frameless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Simon, D.A., Accuracy Validation in Image-Guided Orthopaedic Surgery, Second Annual Intl. Symp. on Med. Rob. an Comp-Assisted surgery, MRCAS '95, pp. 185-192 (undated).

Smith et al., "Computer Methods for Improved Diagnostic Image Display Applied to Stereotactic Neurosurgery," Automedical, vol. 14, 1992, pp. 371-382 (4 unnumbered pages).

Smith et al., "The Neurostation.TM.—A Highly Accurate, Minimally Invasive Solution to Frameless Stereotactic Neurosurgery," Computerized Medical Imaging and Graphics, vol. 18, Jul.-Aug. 1994, pp. 247-256.

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosurgy, vol. 79, pp. 296-303 (Aug. 1993).

The Laitinen Stereotactic System, E2-E6.

Thompson, et al., A System for Anatomical and Functional Mapping of the Human Thalamus, Computers and Biomedical Research, vol. 10, pp. 9-24 (1977).

Trobraugh, J.W., et al., Frameless Stereotactic Ultrasonography: Method and Applications, Computerized Medical Imaging and Graphics, vol. 18, No. 4, pp. 235-246 (1994).

Viant et al., "A Computer Assisted Orthopaedic System for Distal Locking of Intramedullary Nails," Proc. of MediMEC '95, Bristol, 1995, pp. 86-91.

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Weese et al., "An Approach to 2D/3D Registration of a Vertebra in 2D X-ray Fluoroscopies with 3D CT Images," pp. 119-128.

METHOD AND APPARATUS FOR IMPLANTATION BETWEEN TWO VERTEBRAL BODIES

CROSS-REFERENCE TO RELATED APPLICATIONS

This application is a continuation of U.S. patent application Ser. No. 10/837,997, filed on May 3, 2004. The disclosure of the above application is incorporated herein by reference.

FIELD

The present invention generally relates to performing orthopedic surgical procedures, and more particularly, relates to implantation of a device between two vertebral bodies using image guided surgical navigation.

BACKGROUND

Image guided medical and surgical procedures utilize patient images obtained prior to or during a medical procedure to guide a physician performing the procedure. Recent advances in imaging technology, especially in imaging technologies that produce highly-detailed, computer-generated two, three and four-dimensional images, such as computed tomography (CT), magnetic resonance imaging (MRI), isocentric C-arm fluoroscopic imaging, fluoroscopes or ultrasounds have increased the interest in image guided medical procedures. Various imaging devices may include imaging devices such as an O-arm including those disclosed in U.S. Patent Application Publication 2004/0022350, entitled "Breakable Gantry Apparatus for Multidimensional X-Ray Based Imaging"; U.S. Patent Application Publication 2004/0013239, entitled "Systems and Methods for Quasi-Simultaneous Multi-Planar X-Ray Imaging"; U.S. Patent Application Publication 2004/0013225, entitled "Systems and Methods for Imaging Large Field-of-View Objects"; U.S. Patent Application Publication 2003/0235266, entitled "Cantilevered Gantry Apparatus for X-Ray Imaging", each of which is incorporated herein by reference. Furthermore, various other imaging apparatus may include a o-arm apparatus such as those disclosed in U.S. Patent Application Publication 2003/0072416, entitled "Interventional Volume Scanner" and U.S. Pat. No. 6,203,196, entitled "X-Ray Diagnostic Apparatus with a Beam Transmitter and a Beam Receiver Mounted Opposite One Another on a Curved Holder"; each of which is incorporated herein by reference.

During these image guided medical procedures, the area of interest of the patient that has been imaged is displayed on a display. Surgical instruments and/or implants that are used during this medical procedure are tracked and superimposed onto this display to show the location of the surgical instrument relative to the area of interest in the body. Other types of navigation systems operate as an image-less system, where an image of the body is not captured by an imaging device prior to the medical procedure, such as the device disclosed in U.S. patent application Ser. No. 10/687,539, entitled Method And Apparatus For Surgical Navigation Of A Multiple Piece Construct For Implantation, filed Oct. 16, 2003, which is incorporated herein by reference. With this type of procedure, the system may use a probe to contact certain landmarks in the body, such as landmarks on bone, where the system generates either a two-dimensional or three-dimensional model of the area of interest based upon these contacts. This way, when the surgical instrument or other object is tracked relative to this area, they can be superimposed on this model.

Most types of orthopedic medical procedures are performed using conventional surgical techniques that are performed on various parts of the body, such as spine, hip, knee, shoulder, a synovial joint, and a facet joint. These techniques generally involve opening the patient in a relatively invasive manner to provide adequate viewing by the surgeon during the medical procedure. These types of procedures, however, generally extend the recovery period for the patient due to the extent of soft tissue and muscular incisions resulting from the medical procedure. Use of image guided technology in orthopedic medical procedures would enable a more minimally invasive type of procedure to be performed to thereby reduce the overall recovery time and cost of the procedure. Use of the image guided procedure may also enable more precise and accurate placement of an implant within the patient.

The implantation of disc prostheses is an emerging surgical procedure. In order for the disc prosthesis to be optimally functional, it must be placed directly in the disc space between two vertebral bodies. Typically, this position is in the anatomical midline of the spine (i.e., mid-sagittal plane), parallel to the respective vertebral body end plates, with the center of rotation of the disc prosthesis at the center of rotation of the two vertebral bodies. The center of rotation is typically positioned or located at the posterior one-third of the disc space.

However, this type of implant procedure is currently performed using a C-arm fluoroscope to assist the surgeon with placing and aligning the disc prosthesis. During the surgery, the surgeon must judge the mid-line and center of rotation by interpreting images generated from the C-arm. To judge the mid-line, the surgeon or possibly the C-arm operator manipulates the C-arm in the A-P plane, such that a true A-P images is generated, which is generally defined as the spinous process of the vertebral body that equally bisects the two pedicles of the same vertebral body. Once the image is generated, the surgeon will mark the mid-line of the spine, and often place a marker, such as a screw in adjacent vertebral bodies to help guide the placement of the implant. When the disc prosthesis is placed, the surgeon uses these marks to help judge and correct mid-line placement. However, this is time consuming and a tedious step that may not be followed precisely and possibly lead to misplacement of the implant. Moreover, the anterior mid-line mark only denotes the mid-line starting point and does not dictate the mid-line trajectory (i.e. mid-sagittal plane). This trajectory is ultimately left to the skill of the surgeon to determine the final implant trajectory, which is subject to a great amount of variability from surgeon-to-surgeon.

To judge the placement of the disc prosthesis with respect to the center of rotation of vertebral bodies, the C-arm is aligned laterally and fluoroscopic images are obtained during insertion. Once again, the surgeon must use judgment to determine when the disc prosthesis has been inserted posteriorly enough. There are currently no tools available to assist in this judgment available today. Moreover, by requiring the surgeon to take multiple fluoroscopic images, this exposes both the patient and the surgical team to potential undesirable exposure from the fluoroscope. It also requires and takes a significant amount of time to take and analyze these fluoroscopic images, thereby extending the length of the surgical procedure.

Therefore, it is desired to provide a system that allows for substantial navigation and tracking of a prosthesis relative to a portion of the anatomy to ensure that the prosthesis is positioned in a selected portion of the anatomy and a proper orientation, position, and the like, without relying substantially solely on a user's judgment and reducing the number of images required to be taken of a patient.

SUMMARY

A system may be used for both preoperative planning and navigation during an operative procedure. Preoperative planning may be used to plan and confirm a selected procedure and select an implant for performing the procedure. For example, though not intended to be limiting, a selected disc or nucleus implant may be selected depending upon an image acquired of a patient and various measurements, such as size, shape, volume, location in the spine, (cervical, thoracic, lumbar), range of motion, and others, relating to the disc or nucleus to be replaced. The system may also be used to substantially precisely plan and select a placement of an implant. Various other procedures may be performed with the system, such as knee implant selection, a femoral hip stem selection and others. In addition, the system may be used to navigate and perform the procedure to ensure that the selected plan is followed to achieve a result.

According to various embodiments a system to determine a position for implanting a prosthesis in an anatomy is disclosed. The system may be operable with a sensor to navigate a procedure, including a display and a user input. An imaging device may be used to obtain image data of the anatomy for display on the display. The image data is displayed on the display and the user input is operable to define a plurality of points relative to the image data. The system is operable to determine a first anatomical definition relative to the anatomy based substantially only the plurality of points. The first anatomical definition is determined substantially independently of the orientation of the image data.

According to various embodiments a method of selecting a position for a prosthetic to be implanted in an anatomy is disclosed. The method includes obtaining image data of the anatomy and displaying the image data viewable by a user. A plurality of points may be selected or determined on the displayed image data. Also, an anatomical definition may be determined in part due to the defining of the plurality of points.

According to various embodiments a surgical system operable to allow for defining an anatomical definition and navigating a procedure relative to an anatomy is disclosed. The surgical system may include a tracking array to track a position of a sensor and an imaging device operable to obtain image data of the anatomy. A display may be provided to display the image data and a position of a member held relative to the sensor. A user input allows a user to input a first anatomical definition. A processor may process or determine a second anatomical definition. The first anatomical definition and the second anatomical definition assist in the navigating the procedure.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF VARIOUS EMBODIMENTS

The following description of embodiments is merely exemplary in nature and is in no way intended to limit the invention, its application, or uses. Moreover, while the invention is discussed in detail below in regard to orthopedic/spinal surgical procedures, the present invention may be used with any type of medical procedure, including orthopedic, cardiovascular, neurovascular, soft tissue procedures, neuro, or any other medical procedures.

Figure 1:
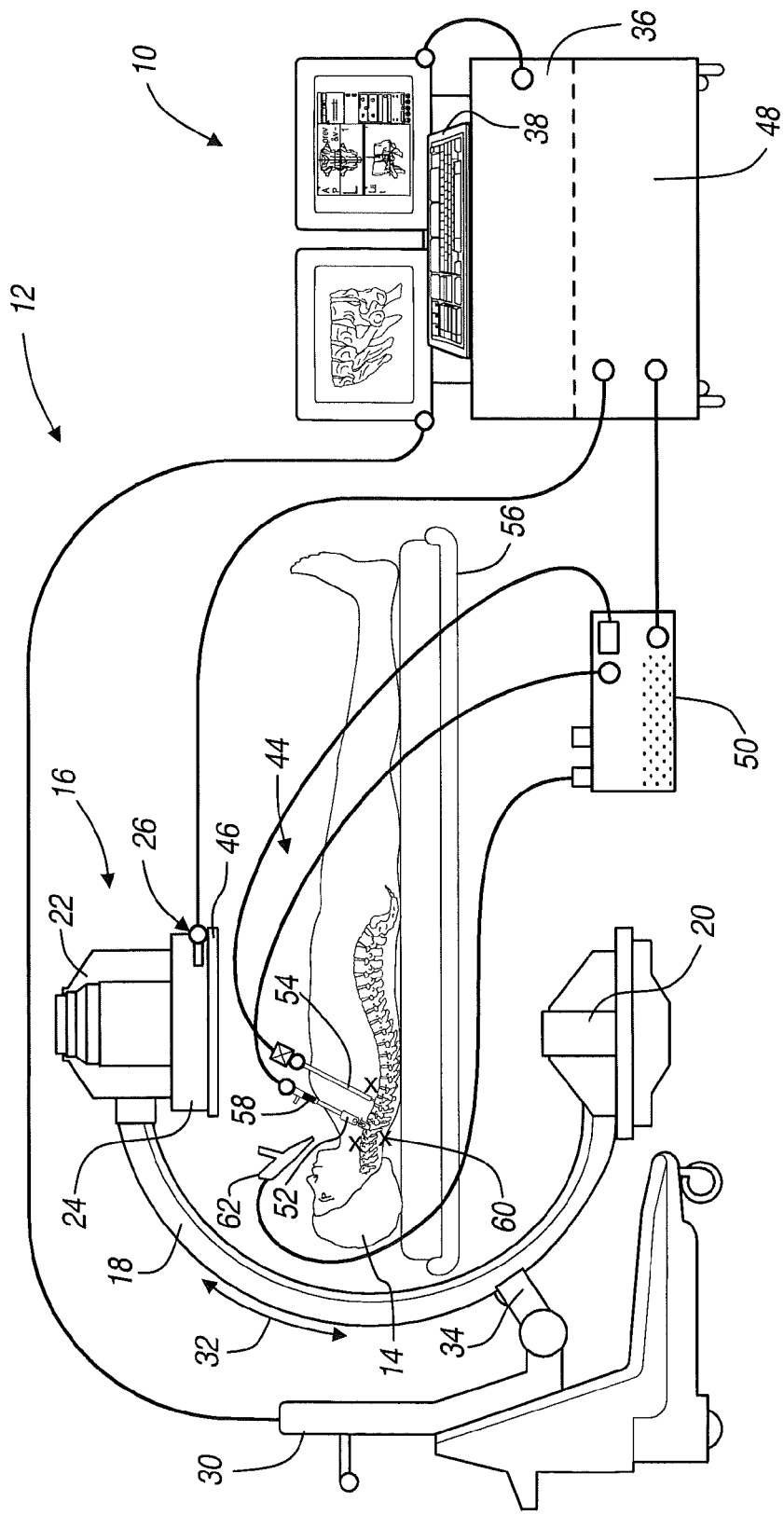
FIG. 1 is a diagram of a navigation system according to the teachings of the present invention.

FIG. 1 is a diagram illustrating a display 10 employed with an image guided navigation system 12 for use in navigating a surgical instrument or implant during a medical procedure. It should also be noted that the display 10 may be used or employed in an image-less based navigation system, further discussed herein. The display 10 may be any conventional display or a display that illustrates a six-degree of freedom display, such as that disclosed in U.S. patent application Ser. No. 10/794,716 entitled "METHOD AND APPARATUS FOR PREPLANNING A SURGICAL PROCEDURE", and filed Mar. 5, 2004, incorporated herein by reference. The navigation system 12 may be used to navigate any type of instrument or delivery system, such as a reamer, impactor, cutting block, saw blade, catheter, guide wires, needles, Rongeur instrument, drug delivery systems, cell delivery systems, and nucleus or disc implant delivery systems. The navigation system 12 may also be used to navigate any type of implant including orthopedic implants, spinal disc implants, interbody implants, fusion devices, nucleus replacement implants, cardiovascular implants, neurovascular implants, soft tissue implants, disc placement devices, or any other devices implanted in a patient 14. In addition to the placement or movement of various implants or instruments, other portions, such as bioactive portions, may be placed or positioned with the procedure. For example, bone morphogenic proteins or other gene therapies may be positioned or implanted relative to selected portions of the anatomy according to various embodiments of the present invention. Therefore, it will be understood that not only macro-devices or implants but micro or mini-bioactive chemicals or portions may be implanted according to various embodiments. The navigation system 12 may also be used to navigate implants or devices that are formed as an assembly or from multiple components where the location and orientation of each component is dependent upon one another to be effective in its use.

The navigation system 12 may include an imaging device 16 that is used to acquire pre-operative or real-time images of the patient 14. The imaging device 16 may be a fluoroscopic imaging device that is incorporated into a C-arm configuration that includes a moveable C-arm 18, an x-ray source 20, an x-ray receiving section 22, an optional calibration and tracking target 24 and optional radiation sensors 26. The optional calibration and tracking target 24 includes calibration markers 28 (see FIGS. 2a-2b), further discussed herein. It will be understood, however, that any appropriate imaging system may be used, including those discussed here.

A controller 30 captures the x-ray images received at the receiving section 22 and stores the images for later use. If a C-arm configuration is used to hold and/or move the imaging system 16, the controller 30 may also control the rotation of the C-arm 18, including the imaging system 16. For example, the C-arm 18 may move in the direction of arrow 32 or rotate about the long axis of the patient 14, allowing anterior or lateral views of the patient 14 to be imaged. Each of these movements involve rotation about a mechanical axis 34 of the C-arm 18. In this example, the long axis of the patient 14 is substantially in line with an axis of motion 34 of the C-arm 18. This enables the C-arm 18 to be moved relative to the patient 14, allowing images of the patient 14 to be taken from multiple directions or about multiple planes. An example of a fluoroscopic x-ray imaging device 16 that may be used as the imaging device is the "Series 9800 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm or O-arm configuration fluoroscopic systems, etc. Generally, in an O-arm configuration, both the transmitter and the receiver are positioned within a substantially annular device or portion such that movement of one portion substantially moves the other portion to keep them substantially opposite one another. Therefore, substantially no resterilization or other procedures may be necessary to use the imaging device. In addition, various other portions may be positioned relative to the imaging device so that they may move with the portions of the O-arm so that their position relative to the transmitter or receiver of the O-arm are known. For example, the signal generator or localizer, for the imaging tracking or navigation system, may be positioned on the O-arm such that movement of the receiving section of the O-arm is known and its position remains substantially constant relative to the generator or localizer portion of the navigation system.

In operation, the imaging device 16 generates x-rays from the x-ray source 20 that propagate through the patient 14 and calibration and/or tracking target 24, into the x-ray receiving section 22. The receiving section 22 generates an image representing the intensities of the received x-rays. Typically, the receiving section 22 includes an image intensifier that first converts the x-rays to visible light and a charge coupled device (CCD) video camera that converts the visible light into digital images. Receiving section 22 may also be a digital device that converts x-rays directly to digital images, thus potentially avoiding distortion introduced by first converting to visible light. With this type of digital imaging device, which is generally a flat panel device, the calibration and/or tracking target 24 and the calibration process discussed below may be eliminated. Also, the calibration process may be eliminated for different types of medical procedures. Alternatively, the imaging device 16 may only take a single image with the calibration and tracking target 24 in place. Thereafter, the calibration and tracking target 24 may be removed from the line-of-sight of the imaging device 16.

As discussed above, various imaging devices, such as an O-arm configuration, may include the x-ray source 20 and the receiving section 22 that are positioned such that they are movable within the O-arm configuration relative to one another without moving the O-arm portion. In this case, the various image generators or signal generators for the tracking system, as discussed herein, may be positioned on the O-arm as well such that movement of the x-ray source 20 and the receiving section 22 substantially move with the signal generator. Therefore, the known or selected position of the generator relative to either the x-ray source 20 or the receiving section 22 remains known and is substantially constant throughout a procedure. This may allow for a single calibration of the generator relative to the receiving section 22 and does not require recalibration of the tracking or generating signal relative to the receiving section 22.

Two dimensional fluoroscopic images taken by the imaging device 16 may be captured and stored in the controller 30. It will be understood that various images may be taken with the various imaging devices 16. For example, in an O-arm configuration, axial or substantially cross-sectional images of the patient may be obtained. Therefore, the various configurations of the imaging devices 16 may allow for substantially complete axial view or cross-sectional view of the patient during an operative procedure or at any other appropriate time. Nevertheless, it will be understood that various other types of images may be obtained for selected purposes and during any appropriate portion of the procedure or substantially pre-operatively. These images may also be forwarded from the controller 30 to a controller or work station 36 having the display 10 that may either include a single display 10 or a dual display 10 and a user interface 38. Alternatively, the images may be forwarded directly to the work station 36. Moreover, other triggers may be used, such as radiation sensors, to provide a trigger to transfer images or image data to the work station 36. The work station 36 provides facilities for displaying on the display 10, saving, digitally manipulating, or printing a hard copy of the received images. The user interface 38, which may be a keyboard, joy stick, mouse, touch pen, touch screen or other suitable device allows a physician or user to provide inputs to control the imaging device 16, via the controller 30.

The work station 36 may also direct the controller 30 to adjust the rotational axis 34 of the C-arm 18 to obtain various two-dimensional images along different planes in order to generate representative two-dimensional and three-dimensional images. When the x-ray source 20 generates the x-rays that propagate to the x-ray receiving section 22, the radiation sensors 26 sense the presence of radiation, which is forwarded to the controller 30, to identify whether or not the imaging device 16 is actively imaging. This information is also transmitted to a coil array controller 48, further discussed herein. Alternatively, a person or physician may manually indicate when the imaging device 16 is actively imaging or this function can be built into the x-ray source 20, x-ray receiving section 22, or the control computer 30.

Figure 2A:
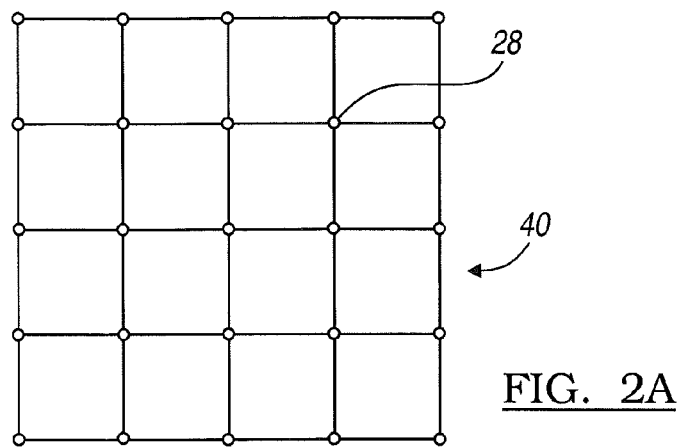
FIGS. 2a, 2b and 2c are diagrams representing undistorted and distorted views of a fluoroscopic C-arm imaging device.
Figure 2B:
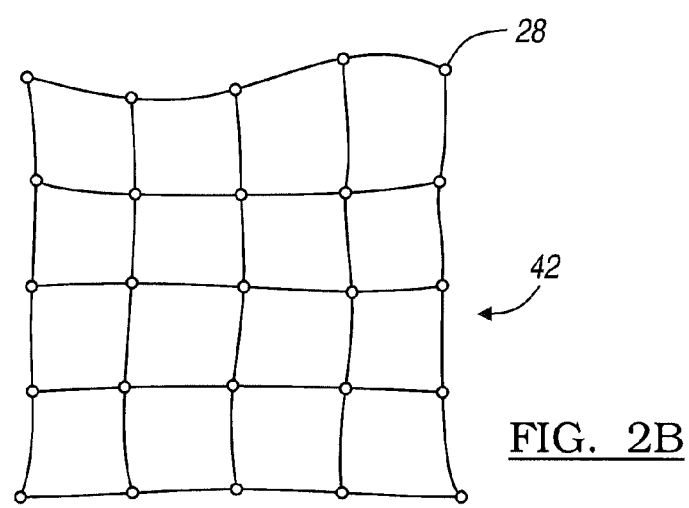

Imaging devices 16 that do not include a digital receiving section 22 may require the calibration and/or tracking target 24. This is because the raw images generated by the receiving section 22 tend to suffer from undesirable distortion caused by a number of factors, including inherent image distortion in the image intensifier and external electromagnetic fields. An empty undistorted or ideal image and an empty distorted image are shown in FIGS. 2A and 2B, respectively. The checkerboard shape, shown in FIG. 2A, represents the ideal image 40 of the checkerboard arranged calibration markers 28. The image taken by the receiving section 22, however, can suffer from distortion, as illustrated by the distorted calibration marker image 42, shown in FIG. 2B.

Figure 2C:
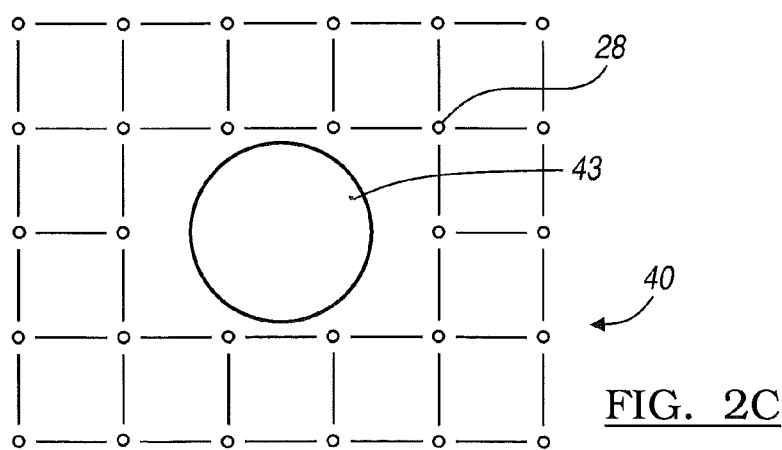

It will be understood that the checkerboard shape that may either be the ideal image 40 or the distorted image 42 may be substantially positioned around an aperture 43 with reference to FIG. 2C. The aperture 43 may allow for a substantial reception of a radiation such as optical or x-ray radiation. Nevertheless, the aperture 43 allows for the various radiations to pass through the selected portions to be received by a receiving section.

Intrinsic calibration, which is the process of correcting image distortion in a received image and establishing the projective transformation for that image, involves placing the calibration markers 28 in the path of the x-ray, where the calibration markers 28 are opaque or semi-opaque to the x-rays. The calibration markers 28 are rigidly arranged in pre-determined patterns in one or more planes in the path of the x-rays and are visible in the recorded images. Because the true relative position of the calibration markers 28 in the recorded images are known, the controller 30 or the work station or computer 36 is able to calculate an amount of distortion at each pixel in the image (where a pixel is a single point in the image). Accordingly, the computer or work station 36 can digitally compensate for the distortion in the image and generate a distortion-free or at least a distortion improved image 40 (see FIG. 2A). A more detailed explanation of exemplary methods for performing intrinsic calibration are described in the references: B. Schuele, et al., "Correction of Image Intensifier Distortion for Three-Dimensional Reconstruction," presented at SPIE Medical Imaging, San Diego, Calif., 1995; G. Champleboux, et al., "Accurate Calibration of Cameras and Range Imaging Sensors: the NPBS Method," Proceedings of the IEEE International Conference on Robotics and Automation, Nice, France, May, 1992; and U.S. Pat. No. 6,118,845, entitled "System And Methods For The Reduction And Elimination Of Image Artifacts In The Calibration Of X-Ray Imagers," issued Sep. 12, 2000, the contents of which are each hereby incorporated by reference.

While the imaging device 16 is exemplary illustrated as a fluoroscopic imaging device in FIG. 1, any other alternative imaging modality may also be used or an image-less based application may also be employed, as further discussed herein. For example, isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), 2D, 3D or 4D ultrasound, intraoperative CT, MRI, or O-arms having single or multi flat panels receivers that move about the ring to acquire fluoroscopic images, may also be used to acquire pre-operative or real-time images or image data of the patient 14.

Image datasets from hybrid modalities, such as positron emission tomography (PET) combined with CT or MRI, or single photon emission computer tomography (SPECT) combined with CT or MRI, could also provide functional image data superimposed onto anatomical data to be used to confidently reach target sights within the areas of interest. It should further be noted that the imaging device 16, as shown in FIG. 1, provides a virtual bi-plane image using a single-head fluoroscope by simply rotating the C-arm 18 about at least two planes, which could be orthogonal planes to generate two-dimensional images that can be converted to three-dimensional volumetric images that can be displayed on the display 10.

The navigation system 12 further includes an electromagnetic navigation or tracking system 44 that includes a transmitter coil array 46, the coil array controller 48, a navigation probe interface 50, an instrument 52 having an electromagnetic tracker and a dynamic reference frame (DRF) 54. It should further be noted that the entire tracking system 44 or parts of the tracking system 44 may be incorporated into the imaging device 16, including the work station 36 and radiation sensors 26. Incorporating the tracking system 44 will provide an integrated imaging and tracking system. Any combination of these components may also be incorporated into the imaging system 16, which again can include a fluoroscopic C-arm imaging device or any other appropriate imaging device.

The transmitter coil array 46 is shown attached to the receiving section 22 of the C-arm 18. However, it should be noted that the transmitter coil array 46 may also be positioned at any other location as well. For example, the transmitter coil array 46 may be positioned at the x-ray source 20, within the OR table 56 positioned below the patient 14, on a movable or positionable cart or device, on siderails associated with the OR table 56, or positioned on the patient 14 in proximity to the region being navigated, such as by the patient's spinal area. The transmitter coil array 46 includes a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The transmitter coil array 46 is controlled or driven by the coil array controller 48. The coil array controller 48 may drive each coil in the transmitter coil array 46 in a time division multiplex or a frequency division multiplex manner. In this regard, each coil may be driven separately at a distinct time or all of the coils may be driven simultaneously with each being driven by a different frequency. Upon driving the coils in the transmitter coil array 46 with the coil array controller 48, electromagnetic fields are generated within the patient 14 in the area where the medical procedure is being performed, which is again sometimes referred to as patient space. The electromagnetic fields generated in the patient space induces currents in sensors 58 positioned in the instrument 52, further discussed herein. These induced signals from the instrument 52 are delivered to the navigation probe interface 50 and subsequently forwarded to the coil array controller 48. The navigation probe interface 50 provides all the necessary electrical isolation for the navigation system 12. The navigation probe interface 50 also includes amplifiers, filters and buffers required to directly interface with the sensors 58 in instrument 52. Alternatively, the instrument 52 may employ a wireless communications channel as opposed to being coupled directly to the navigation probe interface 50. Also, an LC tank circuit may be used to assist in communication and power generation for the instrument 52. Moreover, the various portions may be battery powered rather than require an external or AC circuit.

The instrument 52 is equipped with at least one, and may include multiple localization sensors 58. In this regard, the instrument 52 may include an orthogonal pair coil sensor 58 or a tri-axial coil sensor 58 or multiple single coil sensors 58 positioned about the instrument 52. Here again, the instrument 52 may be any type of medical instrument or implant. For example, the instrument may be a catheter that can be used to deploy a medical lead, be used for tissue ablation, or be used to deliver a pharmaceutical agent, such as BMP, cells, gene therapy, etc. The instrument 52 may also be an orthopedic instrument, used for an orthopedic procedure, such as reamers, impactors, cutting blocks, saw blades, drills, drill guides, distracters, awls, taps, probes, screw drivers, etc. The instrument 52 may also be any type of neurovascular or neuro instrument, cardiovascular instrument, soft tissue instrument, disc placement, nucleus placement, etc. Finally, the instrument 52 may be an implant that is tracked, as well as any other type of device positioned and located within the patient 14. These implants can include orthopedic implants, neurovascular implants, cardiovascular implants, soft tissue implants, spinal implants, nucleus implants, cranial implants, disc implants, or any other devices that are implanted into the patient 14. Particularly, implants that are formed from multiple components where the location and orientation of each component is dependent upon the location and orientation of the other component, such that each of these components can be tracked or navigated by the navigation and tracking system 44 to be displayed on the display 10.

In various embodiments, the electromagnetic sources or generators may be located within the instrument 52 and one or more receiver coils may be provided externally to the patient 14 forming a receiver coil array similar to the transmitter coil array 46. In this regard, the sensor coils 58 would generate electromagnetic fields, which would be received by the receiving coils in the receiving coil array similar to the transmitter coil array 46. Other types of localization or tracking may also be used with other types of navigation systems, which may include an emitter, which emits energy, such as light, sound, or electromagnetic radiation, and a receiver that detects the energy at a position away from the emitter. This change in energy, from the emitter to the receiver, is used to determine the location of the receiver relative to the emitter. These types of localization systems include conductive, active optical, passive optical, ultrasound, sonic, electromagnetic, etc. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The DRF 54 of the electromagnetic tracking system 44 is also coupled to the navigation probe interface 50 to forward the information to the coil array controller 48. The DRF 54 is a small magnetic field detector or any other type of detector/transmitter that is designed to be fixed to the patient 14 adjacent to the region being navigated so that any movement of the patient 14 is detected as relative motion between the transmitter coil array 46 and the DRF 54. This relative motion is forwarded to the coil array controller 48, which updates registration correlation and maintains accurate navigation, further discussed herein. The DRF 54 can be configured as a pair of orthogonally oriented coils, each having the same center or may be configured in any other non-coaxial coil configuration. The DRF 54 may be affixed externally to the patient 14, adjacent to the region of navigation, such as the patient's spinal region, as shown in FIG. 1 or on any other region of the patient. The DRF 54 can be affixed to the patient's skin, by way of a stick-on adhesive patch. The DRF 54 may also be removably attachable to fiducial markers 60 also positioned on the patient's body and further discussed herein. The DRF 54 may also be attached to the OR bed 56. or any other portion, to which the patient 14 is held substantially immobile.

Alternatively, the DRF 54 may be internally attached, for example, to the spine or vertebrae of the patient using bone screws that are attached directly to the bone. This provides increased accuracy since this may track any motion of the bone. Moreover, multiple DRFs 54 may also be employed to track the position of two bones relative to a joint. For example, one DRF 54 may be attached to a first vertebra, while a second DRF 54 may be attached to a second vertebra. In this way, motion of the spine or vertebrae may be detected by the dual DRFs 54. An exemplary DRF 54 and fiducial marker 60, is set forth in U.S. Pat. No. 6,381,485, entitled "Registration of Human Anatomy Integrated for Electromagnetic Localization," issued Apr. 30, 2002, which is hereby incorporated by reference.

The DRF 54 may be affixed or connected to the vertebrae in any appropriate manner. For example, a pin or rod may interconnect the DRF 54 and the vertebrae. Other mechanisms may be provided to reduce rotation, such as teeth or barbs that extend from the rod and further engage the vertebrae that reduce rotation of the rod and the DRF 54. Various exemplary systems are disclosed in U.S. Pat. Nos. 6,226,548 and 6,203,543, each incorporated herein by reference. This may allow the DRF 54 to be attached to the vertebrae substantially percutaneously.

Also the workstation 38, or any appropriate portion of the system, may provide for a check of the placement of the DRF 54 in the image space. For example, unintended rotational or other movement may occur. The system, including software, may be used to determine that at least one of the DRFs 54 have moved. During a cycle of the software, or any other appropriate time, the system may check to ensure that the DRF 54 is in a selected location. If it is not the user may re-register the patient 14. Alternatively a second DRF, of known movement and relative location to the first DRF, may be used to re-register or correlate the inadvertent movement of the first DRF.

Regardless, the system may be able to determine that the DRF is in a location other than a selected or known location. For example, the system may determine that the DRF may have moved an amount greater than expected or a direction, such as rotation about its axis of fixation to the patient, other than one expected. The system, including the workstation 38, may then provide an alert, such as an audible or visual alert, to a user that the unexpected movement has occurred. The user can then re-register the patient 14 or an autonomous re-registration may be completed with the workstation 38.

Briefly, the navigation system 12 operates as follows. The navigation system 12 creates a translation map between all points in the radiological image generated from the imaging device 16 and the corresponding points in the patient's anatomy in patient space. After this map is established, whenever a tracked instrument 52 is used, the work station 36 in combination with the coil array controller 48 and the controller 30 uses the translation map to identify the corresponding point on the pre-acquired image, which is displayed on display 10. This identification is known as navigation or localization. An icon representing the localized point or instrument is shown on the display 10.

In addition, if the DRF 54 includes coils that are tracked with the electromagnetic (EM) tracking system 44. The DRF 54 may include a plurality of coils each placed in a known geometry and distance from each other. Then, during a use of the DRF 54, the system 12 may determine whether interference is obscuring a true measurement of the DRF 54. For example, a metal object may create eddy current induced in the EM coils. Thus the system 12 may both determine a location of the DRF 54 and the relative location of each of the plurality of EM coils in the DRF 54. The system 12 can then compare the relative sensed location and/or placement of each EM coil to the known geometry of the coils and select the most appropriate coil that is providing the most accurate signal. For example, if three coil are placed at a selected angle, such as 120 degrees, and at a known distance, such as 2 mm, from the others this known information can be used to determine which coil is the least interfered. In other words, the coil must be identified closest to its known position relative to the other coils that is currently least interfered with and thus more accurate to use for the DRF signal.

To enable navigation, the navigation system 12 will detect both the position of the patient's anatomy 14 and the position of the surgical instrument 52. Knowing the location of these two items allows the navigation system 12 to compute and display the position of the instrument 52 in relation to the patient 14. The tracking system 44 is employed to track the instrument 52 and the anatomy simultaneously. While the display 10 is configured to show the instrument with six degree of freedom accuracy.

The tracking system 44 essentially works by positioning the transmitter coil array 46 adjacent to the patient space to generate a low-energy magnetic field generally referred to as a navigation field. Because every point in the navigation field or patient space is associated with a unique field strength, the electromagnetic tracking system 44 can determine the position of the instrument 52 by measuring the field strength at the sensor 58 location. The DRF 54 is fixed to the patient 14 to identify the location of the patient 14 in the navigation field. The electromagnetic tracking system 44 continuously recomputes the relative position of the DRF 54 and the instrument 52 during localization and relates this spatial information to patient registration data to enable image guidance of the instrument 52 within the patient 14.

Patient registration is the process of determining how to correlate the position of the instrument 52 on the patient 14 to the position on the diagnostic, pre-acquired, or real-time images. To register the patient 14, the physician or user will select and store particular points from the pre-acquired images and then touch the corresponding points on the patient's anatomy with a tracked pointer probe 62. The navigation system 12 analyzes the relationship between the two sets of points that are selected and computes a match, which correlates every point in the image data with its corresponding point on the patient's anatomy or the patient space. The points that are selected to perform registration are the fiducial arrays or landmarks 60. Again, the landmarks or fiducial points 60 are identifiable on the images and identifiable and accessible on the patient 14. The landmarks 60 can be artificial landmarks 60 that are positioned on the patient 14 or anatomical landmarks 60 that can be easily identified in the image data. Other types of registration may be point registration, contour surface registration, isocentric registration, automatic registration, and any other appropriate system or method of registering a patient space to an image space. The system 12, may also incorporate the system disclosed in U.S. patent application Ser. No. 10/644,680, entitled Method and Apparatus for Performing 2D to 3D Registration, filed Aug. 20, 2003, incorporated herein by reference, to perform 2D to 3D registration by utilizing the acquired 2D images to register 3D volume images by use of contour algorithms, point algorithms, normalized mutual information, pattern intensity, or density comparison algorithms, as is known in the art.

In order to maintain registration accuracy, the navigation system 12 continuously tracks the position of the patient 14 during registration and navigation. This is necessary because the patient 14, DRF 54, and transmitter coil array 46 may all move during the procedure, even when this movement is not desired. Therefore, if the navigation system 12 did not track the position of the patient 14 or area of the anatomy, any patient movement after image acquisition would result in inaccurate navigation within that image. The DRF 54 allows the electromagnetic tracking device 44 to register and track the anatomy. Because the DRF 54 is rigidly fixed to the patient 14, any movement of the anatomy or the transmitter coil array 46 is detected as the relative motion between the transmitter coil array 46 and the DRF 54. This relative motion is communicated to the coil array controller 48, via the navigation probe interface 50, which updates the registration correlation to thereby maintain accurate navigation.

It should also be understood that localization and registration data may be specific to multiple targets. For example, should a spinal procedure be conducted, each vertebra may be independently tracked and the corresponding image registered to each vertebra. In other words, each vertebra would have its own translation map between all points in the radiological image and the corresponding points in the patient's anatomy in patient space in order to provide a coordinate system for each vertebra being tracked. The tracking system 44 would track any motion in each vertebra by use of the DRF 54 associated with each vertebra. In this way, dual displays 10 may be utilized, further discussed herein, where each display tracks a corresponding vertebra using its corresponding translation map and a surgical implant or instrument 52 may be registered to each vertebra and displayed on the display 10 further assisting an alignment of an implant relative to two articulating or movable bones. Moreover, each separate display in the dual display 10 may superimpose the other vertebra so that it is positioned adjacent to the tracked vertebra thereby adding a further level of information on the display 10.

As an alternative to using the imaging system 16, in combination with the navigation and tracking system 44, the display 10 can be used in an imageless manner without the imaging system 16. In this regard, the navigation and tracking system 44 may only be employed and the probe 62 may be used to contact or engage various landmarks on the patient. These landmarks can be bony landmarks on the patient, such that upon contacting a number of landmarks for each bone, the workstation 36 can generate a three-dimensional model of the bones. This model is generated based upon the contacts and/or use of atlas maps. The workstation 36 may also generate a center axis of rotation for the joint or planes, based upon the probe contacts.

Alternatively, the tracking sensor 58 may be placed on the patient's anatomy and the anatomy moved and correspondingly tracked by the tracking system 44. For example, placing a tracking sensor 58 on the femur and fixing the pelvis in place of a patient and rotating the leg while it is tracked with the tracking system 44 enables the work station 36 to generate a center of axis of the hip joint by use of kinematics and motion analysis algorithms, as is known in the art. If the pelvis is not fixed, another tracking sensor 58 may be placed on the pelvis to identify the center of axis of the hip joint. If a tracking sensor 58 is placed on the femur and a tracking sensor 58 is placed on the tibia, upon moving this portion of the anatomy, a center of axis of the knee joint may be identified. Likewise, by placing a separate tracking sensor 58 on two adjacent vertebra and articulating the spine, the center of axis of the spinal region can also be identified. In this way, a target and/or model based on the center of the particular joint may be designated and identified on the display 10. Movement of the instrument or implant 52 may then be tracked in relation to this target and/or model to properly align the instrument or implant 52 relative to the target and/or model.

Figure 3:
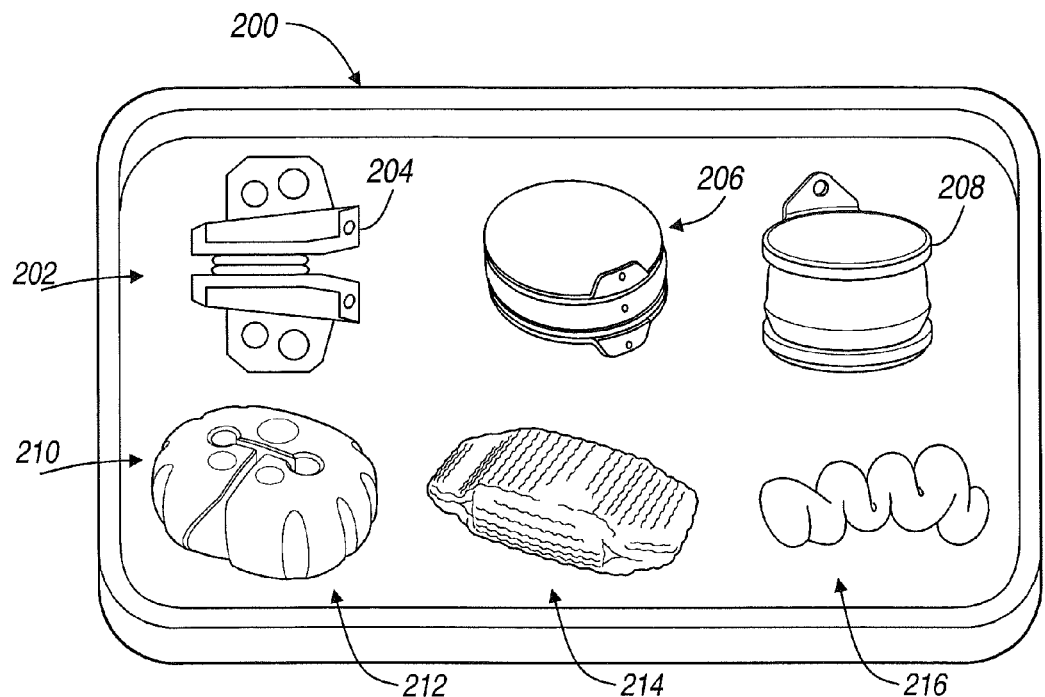
FIG. 3 is a plan view of an exemplary implant kit.

As indicated above, various procedures may be performed with the navigation system 12 where portions of the anatomy may be displayed on the display 10. With reference to FIG. 3, an exemplary implant kit 200 may be provided either pre- or intraoperatively. The kit 200 may include a plurality of implants, which may be used as the implant 52 that may be tracked, from which an implant may be selected. The kit 200 may include a plurality of types and sizes of implants. For example, the kit 200 may include a plurality of disc prosthesis 202. For example, the prosthesis may include a disc prostheses such as a Maverick™ 204, a Bryan™ 206, or a Prestige™ 208 offered by Medtronic Sofamor Danek of Memphis, Tenn. These various types of disc prosthesis 202 may also come or be obtained in a plurality of sizes. Furthermore, the kit 200 may also include a plurality of nucleus implants 210 such as implants described in U.S. Pat. No. 6,620,196, entitled "Intervertebral Disc Nucleus Implants and Methods"; U.S. Patent Application Publication No. 2003/0023311, entitled "Intervertebral Disc Nucleus Implants and Methods, and U.S. Patent Application Publication No. 2003/0199984, entitled "Intervertebral Disc Nucleus Implants and Methods"; the disclosures of each incorporated herein by reference. A shape member nucleus implant 212 may be provided, the implant 212 may be used to replace a selected volume of a nucleus of a disc of the spine. It will be understood that other nucleus prosthesis or implants may be provided such as a prosthesis 214 which may be known as the PDN™ by Raymedica, Inc. of Bloomington, Minn., and described in U.S. Pat. Nos. 5,674,295; 5,824,093; 6,132,465; and 6,602,291, each is incorporated herein by reference.

Figure 4:
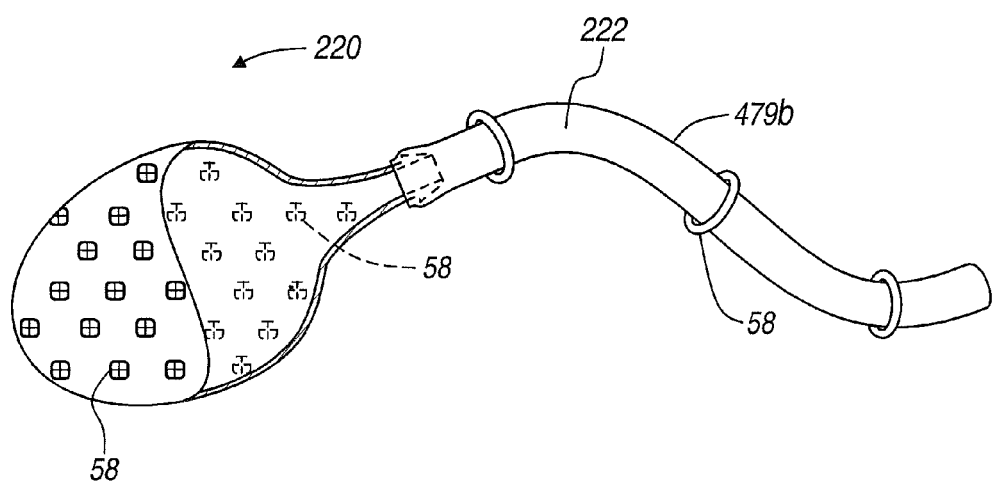
FIG. 4 is a plan view of an implant according to various embodiments that may be included in the kit of FIG. 3.

Alternatively or in addition, a volume filling material such as a braided implant 216 or flowable material may be provided in a bladder implant 220, illustrated in FIG. 4, or alone. The bladder implant 220 may be positioned and filled with a flowable material with an instrument 222. The bladder 220 may include one or a plurality of the tracking sensors 58. Likewise, the instrument 222 may also include one or a plurality of the tracking sensors 58. Therefore, the position of the instrument 222, the position of the bladder 220, the shape of the bladder 220, and size of the bladder 220 may all be tracked, as discussed herein. The tracking may occur for both implantation and verification of a characteristic of the implant. Various flowable materials may be positioned relative to the anatomical portion, such as to replace a nucleus or the disc of a spine. Various implants include those described in U.S. Pat. No. 6,306,177, incorporated herein by reference.

The flowable material may be free flowed into the area of the nucleus or may be flowing into a package which is implanted in the area of the nucleus or the disc. The material that is flowed into the implant may also be substantially cured to achieve selected characteristics, such as a selected rigidity or viscosity. As discussed herein, various instruments may be tracked relative to portions of the anatomy and portions of the implant. For example, the implant package may include tracking sensors such that various portions of the package may be tracked as it is filled with a selected flowable material. A curing source, such as a UV source, can then be tracked relative to the flowable material to determine a selected curing of the material. The curable material may include a characteristic that changes depending upon the amount of curing that occurs. Therefore, the tracking of the UV source or any other appropriate curing source can be used to achieve selected characteristics that are substantially heterogeneous, yet precisely positioned, within the implant.

In addition, according to various other devices, a bladder such as the bladder implant 220 may be formed in any appropriate shape or size. For example, a substantially elongated bladder that includes a length substantially greater than a diameter or width may define a rod. The bladder may then be filled with a selected material for forming a selected configuration, such as a rod, a screw or the like. Therefore, a substantially flexible member may be positioned relative to the anatomy and activated or mixed with a polymer or epoxy to form a substantially hard or rigid rod. Various devices may be used, such as those generally sold by Vertelink Corporation of Irvine, Calif., USA. Moreover, such devices are generally disclosed in U.S. Patent Application Publication 2004/0039305, entitled "Guide-Wire Balloon Modulation Device and Methods of Use"; U.S. Patent Application Publication 2004/0006344, entitled "Expandable Percutaneous Sheath", and U.S. Patent Application Publication 2004/006341, entitled "Curable Media for Implantable Medical Device", each of which is incorporated herein by reference. Therefore, it will be understood that an implant kit or an implant itself may include any appropriate device that may be a substantially pre-formed device or a interoperatively formed device, such as a material that may be cured. The curable material may be positioned inside of a bladder, such as a sheath, or may be positioned relative to the anatomy, such as in a bore formed in the anatomy or any other appropriate position. Therefore, the implant may include any appropriate implant and may be positioned with the system.

As discussed herein a selected characteristic of the implant, such as a position or depth may desired to be tracked and known and may be determined using the various modeling techniques. Therefore, a selected volume of the volume filling implant 216 may be provided to substantially precisely fill the planned removed volume of the nucleus.

Regardless, it will be understood that the kit 200 may provide or include a plurality of various spinal implants. The various implants may either be part of a pre-formed kit or may be pre-selected and determined depending upon various concerns. Therefore, the kit 200 may be substantially customized for a particular procedure because of the implant selected. The kit 200 may also include a plurality of implants from which a selection may be made after the planning and substantially intra-operatively.

These implants or other selected implants are generally positioned in a selected portion of the anatomy to achieve a selected alignment. For example, the navigation system 12 may be used to selectively determine and plan an operative procedure to assure that a selected orientation of the anatomy is achieved. For example, the system 12 may allow for selecting a volume, a position and other elements to achieve a selected outcome of the procedure. Various procedures and methods are known such as those described in U.S. patent application Ser. No. 10/794,716 entitled "METHOD AND APPARATUS FOR PREPLANNING A SURGICAL PROCEDURE", and filed Mar. 5, 2004, incorporated herein by reference.

In addition to substantially selecting an implant that may be positioned to achieve a selected outcome, a method of using the navigation system 12 to assist in positioning an implant, that is selected to achieve a selected result, is disclosed. The navigation system 12 may allow for navigating the spinal implant after determining a selected position in the anatomy relative to which the spinal implant may be placed.

Again, when implanting a spinal disc prosthesis it is desirable for such a prosthesis to function optimally. In order for these prostheses to function optimally, they must be placed directly in the disc space between two vertebral bodies. This position is in the anatomical midline of the spine (i.e., the mid-sagittal plane), parallel to the respective vertebral body end plates, where the center of rotation of the disc prosthesis is at the center of rotation of the two vertebral bodies. The center of rotation is at the posterior portion of the disc space. By positioning the disc prosthesis at the midline and center of rotation, the implant substantially recreates the anatomical motion of the anatomy. It will be understood that determination of a selected position may be formed according to any appropriate portion. For example, a load bearing axis may be determined from a plurality of vertebrae. For example, a load bearing axis may be determined from 4, 8 or any appropriate number of vertebrae. Therefore, the implants may be positioned according to a load bearing axis of the spine, in addition to an axis of rotation of two adjacent or selected vertebrae. Therefore, it will be understood that the midline or any appropriate axis such as the load bearing axis may be found or determined with the system for implantation of the selected implant.

Types of implants can include disc prosthesis implants, inner body fusion devices, nucleus replacement devices or any other devices that are implanted in a space between two or more vertebral bodies. Moreover, in a substantially minimally invasive procedure, it may be desirable to allow for determining of the position of the anatomy without providing an intrusive procedure that requires an extensive surgical dissection. The various minimally or less evasive procedures may allow for substantial retention of selected soft tissue, such as the muscle tissue. Therefore, the less or minimally invasive procedures may allow for positioning instruments substantially percutaneously or through an incision yet without disturbing various muscle bundles or groups. That is, the instruments may be passed relative to the various muscle bundles without separating the muscle bundles or groups to allow for substantial reduced trauma or injury thereto. This may preserve muscle tissue and other soft tissues to reduce healing time after a selected procedure and increase patient satisfaction.

It will be understood that although the following description relates generally to the implantation of a disc prosthesis in a spinal portion of the anatomy of the patient 14, any other appropriate prosthesis may be used with the below described system or method. For example, various intervertebral implants such as nucleus and other devices may be positioned with the system and method. Implants and prostheses that affect the disc space and also those that may provide for interbody fusion may also be used. In addition, various other procedures, such as other orthopaedic procedures including hip implants, knee implants, humeral implants and the like may be implanted using the system. As discussed herein, the system and method generally allows for determining a selected anatomical definition, which may include various points and planes, as further described herein according to various embodiments. Such as various planes and the like, to allow for ensuring that a prosthesis is positioned relative to a selected portion of the anatomy in a selected manner.

Figure 5:
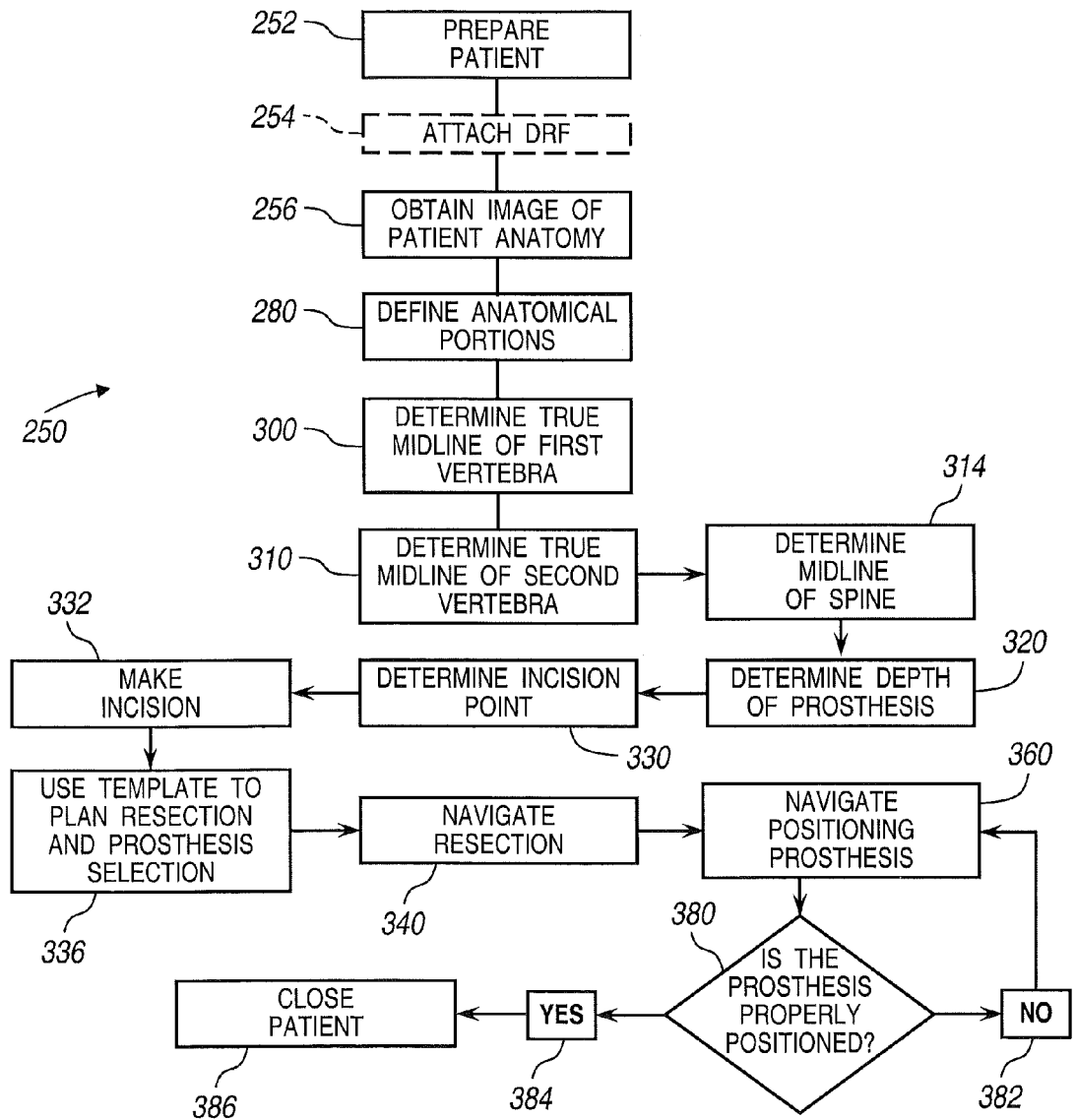
FIG. 5 is a logic block diagram illustrating a method of positioning an implant according to various embodiments.

With reference to FIG. 5, a method of performing a surgical procedure 250 is defined. Initially, the patient 14 is prepared for the procedure 250 in block 252. For example, the patient 14 may be positioned in an operating theatre, such as in an operating room, and positioned on the table 56 which may be substantially radiolucent for use of selected imaging devices 16. For example, the imaging device 16 may include a fluoroscope which is positioned on the C-arm 18. Nevertheless, the imaging device may be any appropriate imaging device or modality, such as a CT, MRI, 3-D, ultrasound, PET, 2-D to 3-D image matching and other appropriate methods. Regardless, the patient is prepared in block 252 for performing the method 250.

After the patient is prepared for the procedure in block 252, the DRF 54 may be affixed to a selected portion of the patient's 14 anatomy. The DRF may be attached in block 254 as a substantially optional procedure. As discussed herein, the DRF 54 may assist in substantially allowing a real time registration and tracking of the patient's anatomy relative to the image space. Therefore, the patient space, including the location of various instruments and implants relative to the patient's anatomy may be substantially real time tracked using the system 12 on the display 10. The DRF 54 may be attached in any appropriate location, such as to dermis of the patient, substantially percutaneously relative to a selected portion of the spine, such as vertebrae of interest, to the pelvis or to a portion of anatomy remotely therefrom. Regardless, DRF 54 may allow for substantially real time tracking of the patient space to the image space.

It will be understood, however, that attaching the DRF 54 is not necessary. For example, the patient may be substantially fixed in a relative location such that once registering of the patient relative to the image space, the patient substantially does not move. This allows the image on the display 10 to accurately show the relative location of the instrument 52 relative to the patient's anatomy.

Figure 6:
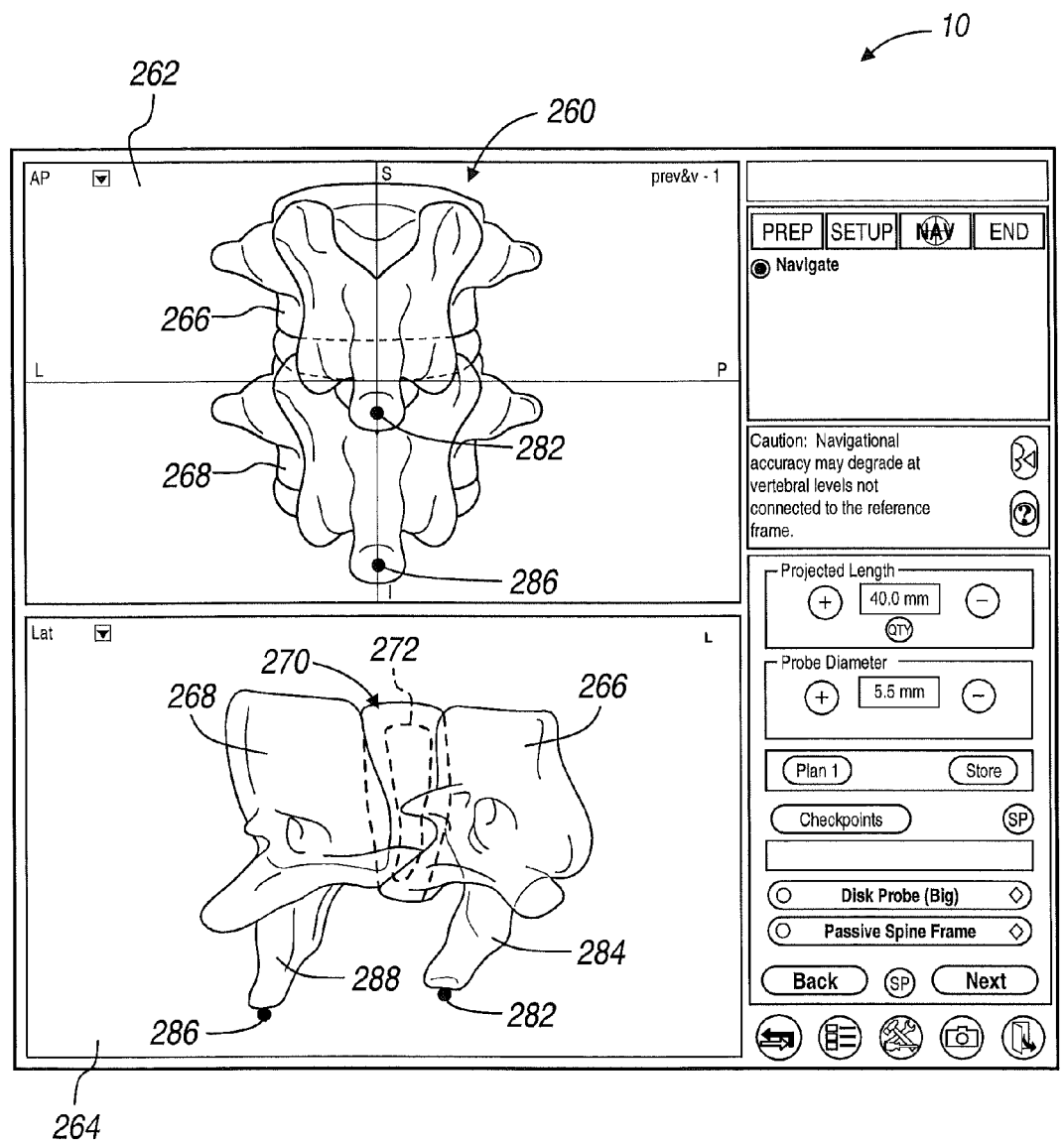
FIG. 6 is a view of a display displaying image data for selecting anatomical points.
Figure 7:
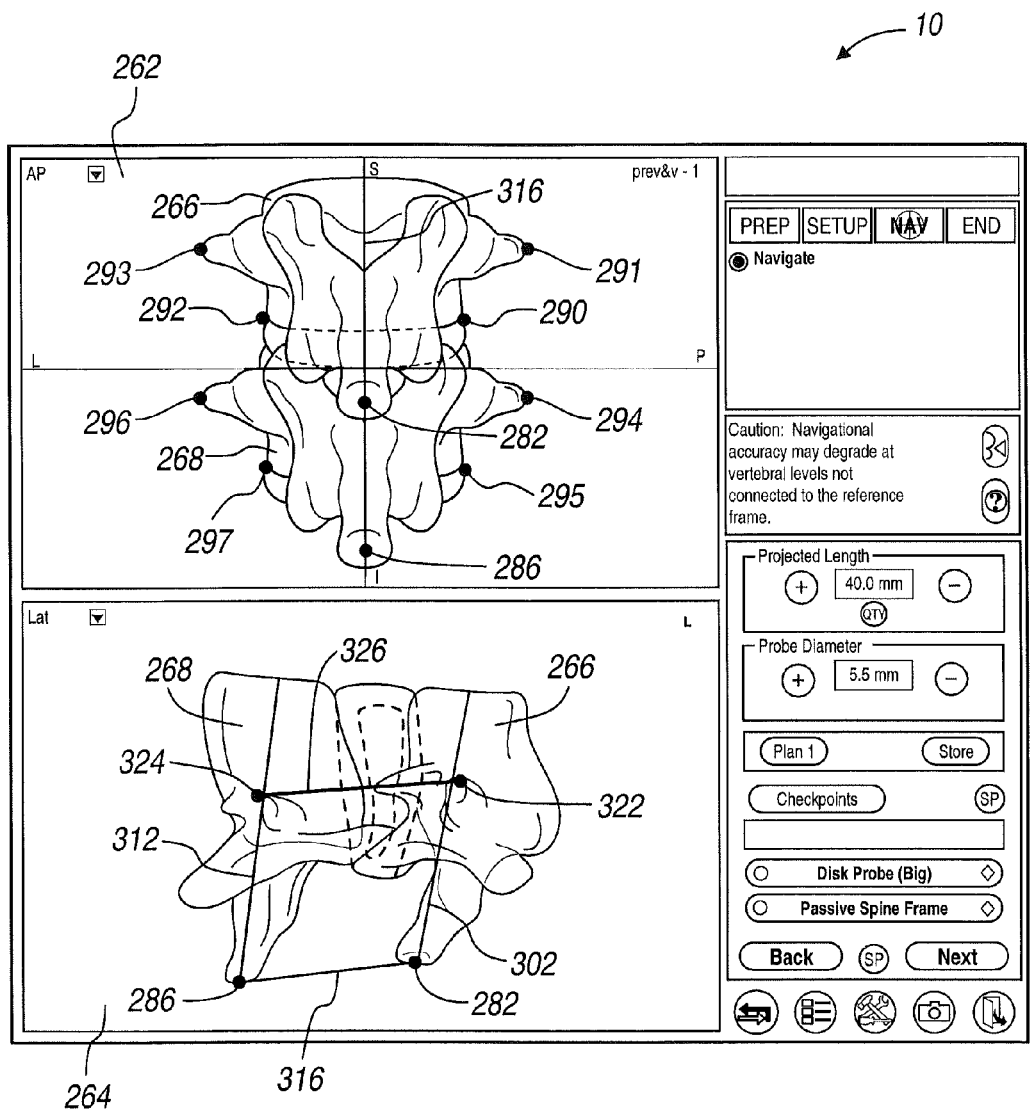
FIG. 7 is a display for displaying image data and illustrating a determined anatomical definite.

After optionally attaching the DRF 54, or at any appropriate time, obtaining an image of the patient 14 occurs in block 256. The images obtained of the patient 14 may be displayed on the display 10, as illustrated in FIG. 6. The images obtained of the patient 14 may be any appropriate images and may vary depending upon a selected procedure. Nevertheless, on the display 10 a selected anterior/posterior plane image (AP) 262 and a lateral plane image (LAT) 264 of the patient 14 may be produced. The display 10 may then display the view of a spine 260 as the AP view 262 and the lateral view 264. The various views 262, 264 may be displayed on the display 10 such that a user may view the images of the spine 260.

As discussed above, various user inputs 38 may be provided such that the user may perform procedures relative to the views 262, 264 of the spine 260 on the screen 10. In addition, it will be understood that the spine 260 is not the only portion of the patient that may be displayed on the display 10. For example, various other portions of the anatomy including a femoral portion, a humeral portion and the like may be displayed on the screen for a various procedures. Nevertheless, the following discussion relates generally to an implantation of a disc prosthesis and, therefore uses various views of the spine 260. Regardless, the images obtained in block 256 may be displayed on the screen 10 for viewing by the user.

Generally, the image of the spine 260 includes at least an image of a first vertebra 266 and a second vertebra 268. Generally, the vertebrae 266, 268 are separated by a disc 270 that may be replaced in a procedure. The disc 270 generally includes a nucleus 272 that may also be replaced according to various embodiments. As is known and discussed herein, the user inputs 38 may be used in conjunction with the images 262, 264 to obtain data regarding the spine 260 or define points thereon, as discussed herein according to various embodiments. For example, various dimensions, sizes, and the like may be determined on the display 10.

It will be understood that the images displayed on the screen 10 may be taken substantially pre-operatively, although after the patient 14 is positioned relative to the system 12. Therefore, the images 262, 264 may be obtained of the patient 14 prior to forming an incision in the patient 14 to begin the operative procedure.

With continuing reference to FIGS. 5 and 6, after the images of the patient 14 are obtained in block 256 and displayed on the screen 10, portions of the anatomy may be defined on the screen 10 by a user in block 280. As discussed herein, the procedure relates to a disc implant in the spine 260, therefore specific examples relating to identifying portions of the spine 260 are discussed. Nevertheless, it will be understood that various portions of the anatomy other than spinal portions may be identified with the system 12.

The system 12, using the user's input 38, can be used to identify a first point 282 on a first spinous process 284 on the first vertebra 266 and a second point 286 on a second spinous process 288 on the second vertebra 268. The user may use the user interface 38 that includes a touch screen on the screen 10, a mouse, a keyboard, a pen, other pointer, or the like to identify the respective spinous process points 282, 286. Regardless, the spinous processes points 282, 286 may be identified and stored in the workstation 36 for later use. The points 282, 286 may be identified on the various views 262, 264 of the spine 260 to assist the workstation 36, or other appropriate system, in determining various portions of the anatomy or anatomical definitions relative to the spine 260.

It will be understood that any appropriate mechanism may be used to determine various points or portions of the anatomy, such as the first point 282 and the second point 286. For example, a computer utilizing a selected algorithm or program may be used to selectively automatically choose or determine the position of the various points 282, 286. Therefore, the images that are obtained may be used by a processor, utilizing the various algorithms or programs, may selectively determine the positions of the points that may be used to determine the various axes and planes as discussed herein. Therefore, it will be understood that the determination of the points 282, 286 or any appropriate points may be done substantially manually by a user or substantially automatically by a computer or processor.

In addition to providing a substantially automatic determination of various points, such as the spinous process point 282, 286, a partial or semi-automatic determination may also be made. For example, an atlas model may include points that are already determined on the atlas model. Then the images of the patient may be obtained using the selected imaging device 16 and they may be substantially coordinated or registered with the atlas images. Therefore, a user or a processor may use the predetermined or best points on the atlas model and correlate them with positions or points on the images of the anatomy and the atlas model may be morphed relative to the anatomy. Therefore, the points that are predetermined in conjunction with various planes and axes on the points in the atlas model are coordinated with the patient and these may be morphed to the anatomy of the patient 14. The images of the anatomy of the patient 14 obtained with the imaging device 16 allows for morphing of the images relative to the atlas model to allow for an efficient determination of selected planes and axes.

Therefore, rather than requiring the processor to substantially independently determine the selected axes and planes, the atlas model already including the selected points that define the various axes and planes may be morphed relative to the anatomy of the patient substantially intra- or pre-operatively. Regardless, it will be understood that the various points may be determined in any appropriate manner, substantially automatically or manually. Also, the various axes and planes may be determined therefrom either intraoperative or preoperatively.

After the relative spinous process points 282, 286 are defined, further anatomical portions may be defined in block 280. For example, a plurality of vertebral portions, including symmetrical lateral portions, on each of the vertebrae 266, 268 may be defined. For example, a first vertebral body lateral point 290 and a second vertebral body lateral point 292 may be defined on the first vertebra 266. Also on the first vertebra 266, a first lateral transverse process point 291 and a second lateral transverse process point 293 may be defined. Similarly, on the second vertebra 268 a first lateral transverse process point 294 and a second lateral transverse process point 296 in addition to a first vertebral body lateral point 295 and a second vertebral body lateral point 297.

The various lateral points 290-297 may be defined on the vertebrae 266, 268 relative to the disc 270 that is to be repaired or replaced. Therefore, defined on the screen 10 and in the workstation 36, are a plurality of points identified by the user using the user input 38 that may be used by the workstation 36, and algorithms and software included therein, to identify various anatomical definitions.

Using these points 290-297 and any other appropriate points, a true midline may be determined in block 300. The true midline determined in block 300 may be determined substantially alone with the workstation 36 using various known trigonometry algorithms or calculations or the true midline may be defined in conjunction with the user. Therefore, the workstation 36 using the inputs provided by a user, may substantially determine the true midline in block 300 substantially automatically or without further input from a user, although the user may further assist in defining the true midlines determined in block 300, which may be an anatomical definition. Therefore, it will be understood that the method 250 may allow for determining a true midline in block 300 substantially automatically with the user substantially only defining various points of the anatomy.

Regardless, the various points 290-297 may be used to substantially define a first midline 302 on the display 10 of the first vertebra 266. A midpoint of the transverse process may be defined as an intersection of a line between each of the identified lateral transfer process points 294, 296 and substantially normal to a line though the spinous process point 286. A line through relative spinal process point 286 and the mid point substantially define the true midline 302.

After determining the first midline 302 for the first vertebra 266, a second determined true midline 312 for the second vertebra 268 can be determined in block 310. The second true midline 312 may then be defined relative to the second vertebrae 268 using the same process as described regarding the first vertebra 266 except for the points relative to the second vertebra 268.

Therefore, the system 12, either alone or in conjunction with a user, can define both the first midline 302 in block 300 and the second midline 312 in block 310 to produce two midlines of the respective vertebrae 266, 268. These two midlines 302, 312 may then be used to produce an anatomical definition including a midline plane 316 (i.e., mid-sagittal plane) of the spine 260 in block 314. The midline plane 316 may then be defined on the screen 10 as a connection between the first midline 302 and the second midline 312. The spinal midline 316 may then be illustrated on the screen 10 relative to the spine 260. The spinal midline 316 may be used for orienting and placing the selected prosthesis, such as the disc prosthesis, relative to the spine 260.

Because the images 262, 264 are obtained of the patient 14 substantially during an operative procedure, the true midline 316 of the spine 260 can be determined using the specific anatomical structures of the spine 260 and the views obtained of the patient 14 during the operative procedure or pre-operatively. The images obtained of the patient 14 may also include any appropriate images. For example, substantially weight bearing or standing images of the patient 14 may be obtained with various images devices 16, such as an O-arm configuration. Therefore, the patient 14 may be positioned in a substantially weight bearing position such that the images may be obtained of the spinal region or any appropriate region to obtain a substantially accurate weight bearing axis of the spine. The images obtained may be either 2-D, 3-D or any appropriate dimensions required or selected for the procedure. Therefore, it will be understood that the images obtained of the patient may be any appropriate images and may be any images selected to achieve or perform the selected procedure. Therefore, the midline 316 of the spine 260 may be substantially a determined midline of the spine or a substantially weight bearing midline or axis of the spine, according to selection by the user. Regardless, the system, including the tracking and navigation system 12, allows for a substantial precise determination of the spinal midline 316 for substantially precise positioning of the disc prosthesis. It will be understood that if the AP image 264 is not a true AP image of the spine 260, the spinal midline 316 may be generated substantially obliquely relative to the AP image 264. Therefore, regardless of how the image of the spine 260 is obtained and displayed on the display 10, the system 12 including the work station 36 and any appropriate software as will be understood by one skilled in the art, may produce a substantially true midline 316 for performing the procedure.

In addition to determining a selected axis, such as an axis of rotation or a weight bearing axis, either automatically or semi-automatically, the axis may be redefined. Therefore, the various points of the spine may be used to determine a selected axis or plane of the spine. However, after review by a user, such as a surgeon, it may be determined that the axis or the view of the spine is not a selected view. Therefore, images of the patient may be re-obtained and the various points and axes re-determined and re-selected to allow for an iterative process to determine the best view or plane of the patient. Therefore, it will be understood that the process of determining the selected points and axes need not be a substantially single step or unaugmentable procedure. A user or the processor may determine points and determine an axis and upon review further determine that the image is not the appropriate image. The user or the system may determine that additional images may be taken of the patient to assure that the image and the axes determined are substantially correct. Thus, the user or the system may reobtain images and reselect the various points and determine the various axes and planes to ensure that the appropriate axes and planes and the appropriate views are obtained.

In addition to determining the true midline of the spine 316, a depth of positioning the disc prosthesis may also be determined in block 320. For example, a first depth point 322 on the first vertebra 266 may be substantially indicated on the lateral view 262. A similar depth point 324 may be selected on the second vertebra 268. The first and second depth points 322, 324 may be used by the workstation 36 to generate a depth plane 326 through the two points 322, 324 that is substantially normal to the spinal midline plane 316. The depth plane 326, of the points 322, 324 alone, may be used by the user to navigate the implant to ensure that the implant is positioned to a selecting depth. Therefore, the depth plane 326 may be used to ensure that the implant is positioned in a selected portion of the spine 260 to achieve a selected result The system, including the work station 36, may use the points inputted by a user, such as a surgeon, with the user input device 38 to substantially calculate the connection of the two points 322, 324 to define the depth plane 326 that is substantially normal to the spinal midline 316. Nevertheless, it will be understood that the user may again intercede and assist in producing the depth plane 326 to ensure that the system substantially correctly defines the plane. In addition, the two depth points 322, 324 assist the user in ensuring that the prosthesis is only inserted to a selected depth, as discussed herein.

As discussed above, the various anatomical definitions, including midline plane 316 and the depth plane 326, may be produced substantially before beginning the invasive portion of the procedure. Therefore, the system 12 may also assist in substantially determining an appropriate incision point on the patient 14 determined in block 330. The determined incision point in block 330 may be determined substantially relative to the vertebrae 266, 268. The determined incision point may allow for a reduced trauma to the patient 14 by ensuring that the incision is positioned substantially near the area where the disc prosthesis is to be implanted. For example, the incision may be substantially determined to be directly centered and co-linear with the disc 270 that is to be replaced.

It will be understood that the steps of determining the true midline 302 of the first vertebra in block 310, determining the true midline 312 of the second vertebra in block 310, determining the midline of the spine 316 in block 314 and determining a depth plane 326 in block 320 may substantially be a sub-routine that may differ based upon a selected procedure. As discussed above, the exemplary procedure relates to a disc prosthesis implantation relative to the spine 260. Nevertheless, it will be understood that various other planes, lines and the like may be determined for other portions of the anatomy depending upon the specific procedure to be performed.

After the incision point is determined, the incision may be made in block 332. The incision may substantially expose the portion of the anatomy regarding the procedure. Nevertheless, due to the navigation system 12, the incision may be substantially minimal to reduce trauma to the patient 14.

Figure 8:
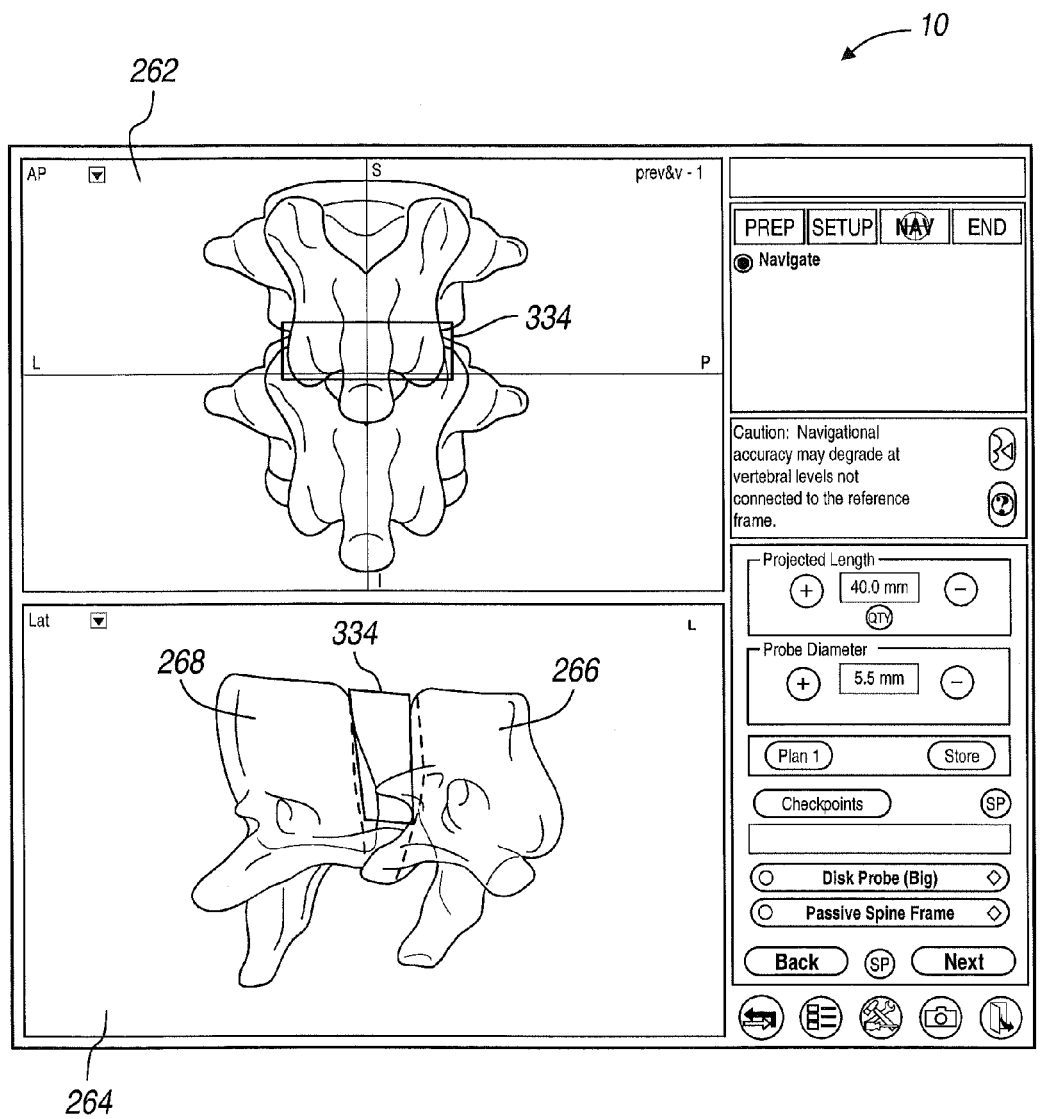
FIG. 8 is a display displaying image data including a template of an implant according to various embodiments.

Also, at any appropriate time, a planning procedure may occur wherein, with reference to FIG. 8, a template 334 is positioned relative to the vertebral 266, 268 in block 334. The use of the template in block 336 may be for any appropriate purpose. For example, the template 334 may be displayed on the screen 10 relative to the vertebrae 266, 268. The template 334 may then be used to select a prosthesis to substantially fill the area where the disc 270 presently exists. The template 334, in conjunction with the images, may be used to ensure that the vertebral 266, 268 are positioned with a selected prosthesis in a selected manner. In addition, the template 334 may assist in selecting a prosthesis to substantially achieve the selected anatomical position. The user of the template 334 is described in U.S. patent application Ser. No. 10/794,716, entitled "METHOD AND APPARATUS FOR PREPLANNING A SURGICAL PROCEDURE", filed Mar. 5, 2004, and is incorporated herein by reference.

After the template 334 has been optionally used to select an appropriate amount of resection and a selected implant, the system 12 may be used to substantially navigate a procedure in block 340. In navigating the procedure in block 340, a resection may be navigated. To assist a resection the vertebrae 266, 268 may be substantially distracted. Therefore, after the distraction of the vertebrae 266, 268, the views 262, 264 may be substantially updated to ensure that the images 262, 264 properly indicate the position of the vertebrae 266, 268 relative to each other and the instrument 52. It will be understood that if the DRF 54 is positioned relative to the patient 14, such as fixed to either one or both of the vertebrae 266, 268, the work station 36 may substantially automatically update the position of the relative portions of the anatomy and relative to the instrument 52 and manual re-registration is not required. Nevertheless, it will be understood that such re-registration may occur to assist in the procedure.

The instrument 52 may be any appropriate instrument that includes the sensor 58. As discussed above, the sensor 58 may be any appropriate sensor such as an electromagnetic sensor (EM), optical sensor, acoustic sensor, radiation sensor and the like. Regardless, the sensor 58 allows for the array 46 to substantially track the instrument 52 with the tracking system 44 such that the position of the instrument 52 may be displayed on the screen 10 relative the spine 260. Therefore, the instrument 52 may be navigated relative to the spine 260 to allow for a substantial precise following of a selected procedure including removing a selected portion of the disc 270. Therefore, it will be understood that the navigation of the resection of block 340 may be used to substantially track instruments to ensure that the resection follows the substantially planned procedure to remove a selected portion of the disc 270.

Figure 9:
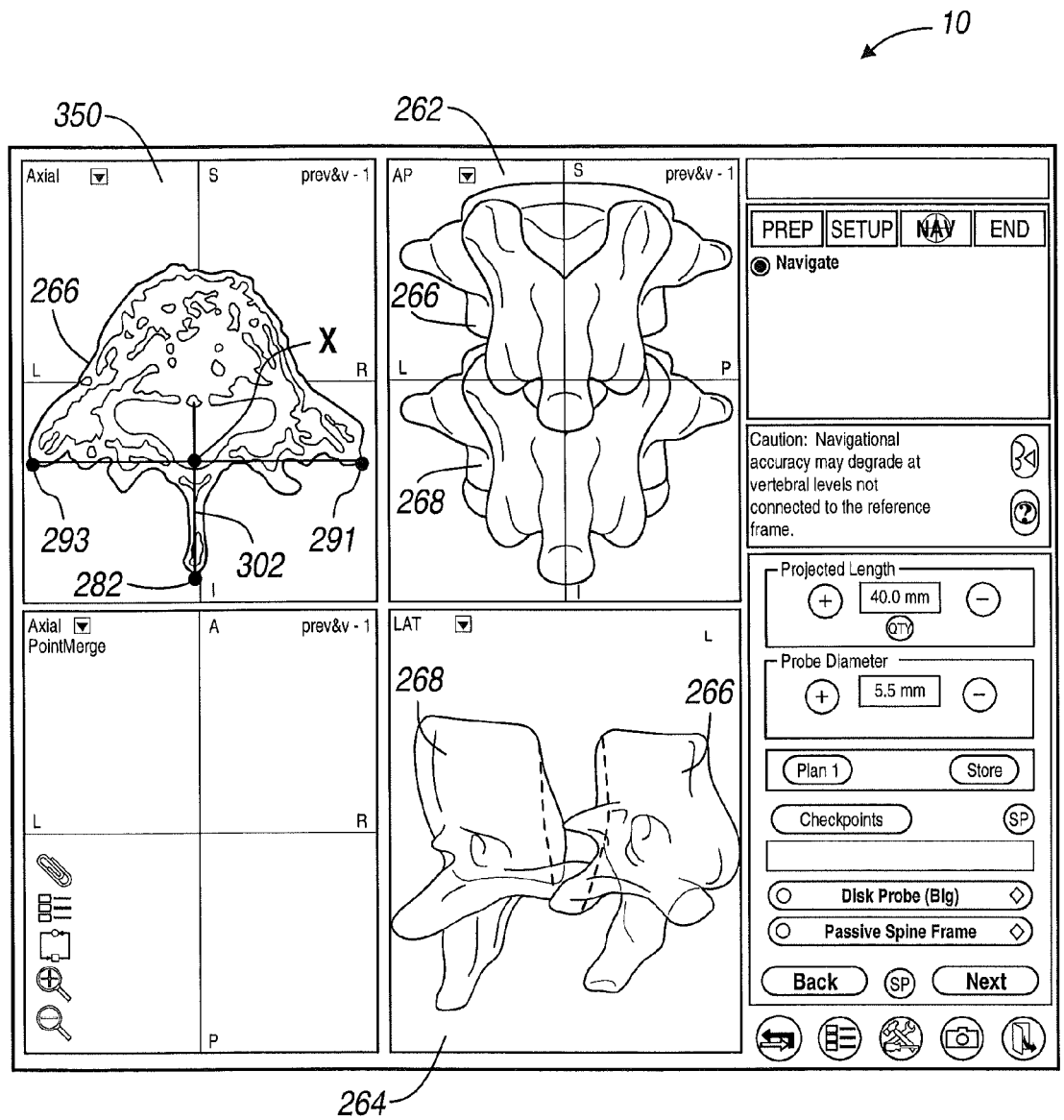
FIG. 9 is a display displaying image data including a determined anatomical definition.

It will be understood that, with reference to FIG. 9, various other views of the spine 260 including the first vertebrae 266 may be obtained. In addition to the AP view 262 and the lateral view 264, a substantially axial view 350 may also be produced. The axial view 350 may be produced using selected imaging devices such as 3-D imaging, including CT scanning, MRI scanning and other appropriate imaging devices. These devices may allow for substantially forming the axial view 350 to obtain an axial view of the vertebrae 266 and other various portions of the anatomy including the second vertebrae 268 and other portions.

As discussed above, a plurality of points may be defined on the axial view 350 including the spinal process point 282, the lateral transverse process points 291 and 293 for determining the various anatomical definitions, such as a midpoint X. The midpoint X may be substantially defined as the point substantially in the middle of a line between the lateral transverse points 291, 293. It will be understood that the midpoint X may be substantially determined by the system or may be defined by a user. In addition, the true midline 302 of the first vertebrae 266 is substantially defined as a line through the midpoint X and the spinal process point 282. Therefore, it will be understood that a plurality of views of the anatomy including the spine 260 may be produced to assist in determining the various anatomical definitions including the spinal midline 316 and other portions.

These various additional lines and views may also assist a user in navigating the resection in block 340 and in a navigation of the positioning of the prosthesis in block 360. Initially, it will be understood that the prosthesis for implantation may be tracked in any appropriate manner. For example, the prosthesis may include one or a plurality of the sensors 58 which may include any appropriate sensor. For example, the sensors 58 may include EM sensors that are positioned in the prosthesis such that the position of the prosthesis may be determined. A plurality of the sensors may be positioned in the prosthesis to allow for a substantially precise determination of each of the portions of the prosthesis during the implantation. As discussed above, various implants may include a substantially inflatable portion that is selected to increase in size during an implantation. In addition, the sensors 58 may include optical sensors, acoustic sensors, and the like.

Various sensors may be connected to the prosthesis such that the position of the sensor 58 may be used by the tracking system 44 to determine a position of the prosthesis relative to the sensor 58. Therefore, the sensor 58 may be substantially removably interconnected with the prosthesis during the procedure to allow for tracking the position of the prosthesis relative to the anatomy for display on the display 10 and, after implantation is completed, the sensor 58 may be removed. Alternatively, the instrument 52 may be affixed to the implant during the procedure so that the implant may be tracked and displayed on display 10, via the instrument 52.

Figure 10A:
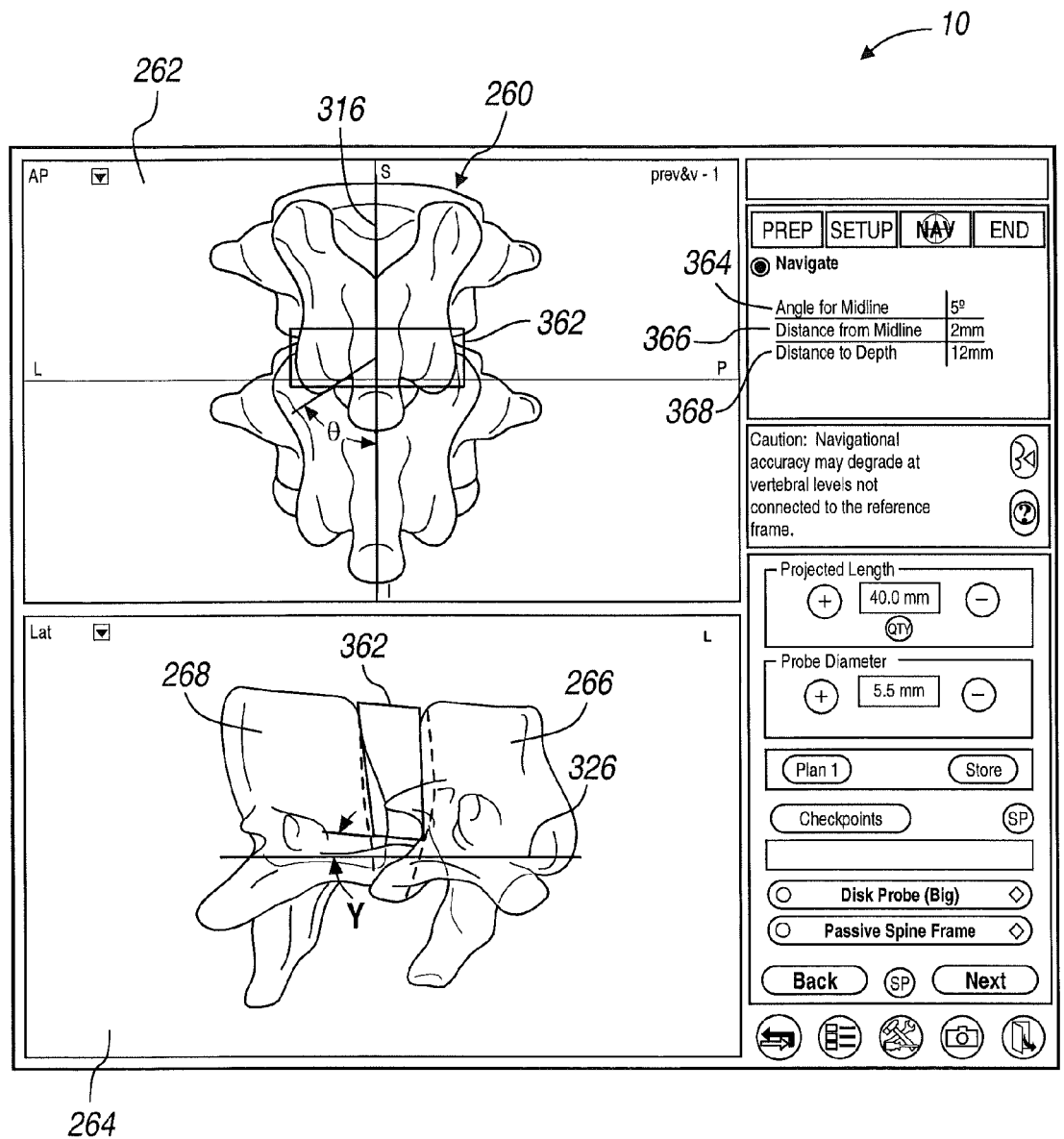
FIG. 10A is a display displaying image data for navigating an implantation relative to the display.

With reference to FIG. 10A, the midline plane 316 may be illustrated on the display 10 relative to the spine 260. In addition, the depth plane 326 may also be illustrated. The position of the prosthesis may be illustrated as an icon 362 on the display 10. Therefore, the position of the prosthesis illustrated as the icon 362 can be navigated with the system 12 and a position known by the user relative to the midline plane 316 and the depth plane 325. Therefore, the position of the implant can be substantially precisely positioned relative to at least these two planes during the positioning of the implants relative to the spine 260. It will be understood that various other portions of the anatomy may be illustrated and the position of the implant may be determined. Regardless, the image 10 may be used by a user to assist in positioning the implant relative to the vertebrae 266, 268.

In addition to displaying the implant 362, various other cues, instructions, or navigational elements may be displayed. For example, numerical determinations such as an angle from the midline 364, a distance from the midline 366, and a distance from the selected depth 368 may be illustrated on the display 10. In addition, various other numerical portions of data may be illustrated relative to the spine 260 based upon the determined or sensed position of the implant 362. Moreover, various graphical cues may be provided on the display 10 such as an "angle of attack $\phi$ which may generally relate to the angle from the midline number 364. A user may graphically understand the distance from the selected midline plane 316 and a distance Y from the depth plane 325. This allows the user to graphically and numerically determine the present position of the implant illustrated as the icon 362 relative to a selected position of the implant including the position of the implant relative to the midline 316 and the depth plane 325.

Figure 10B:
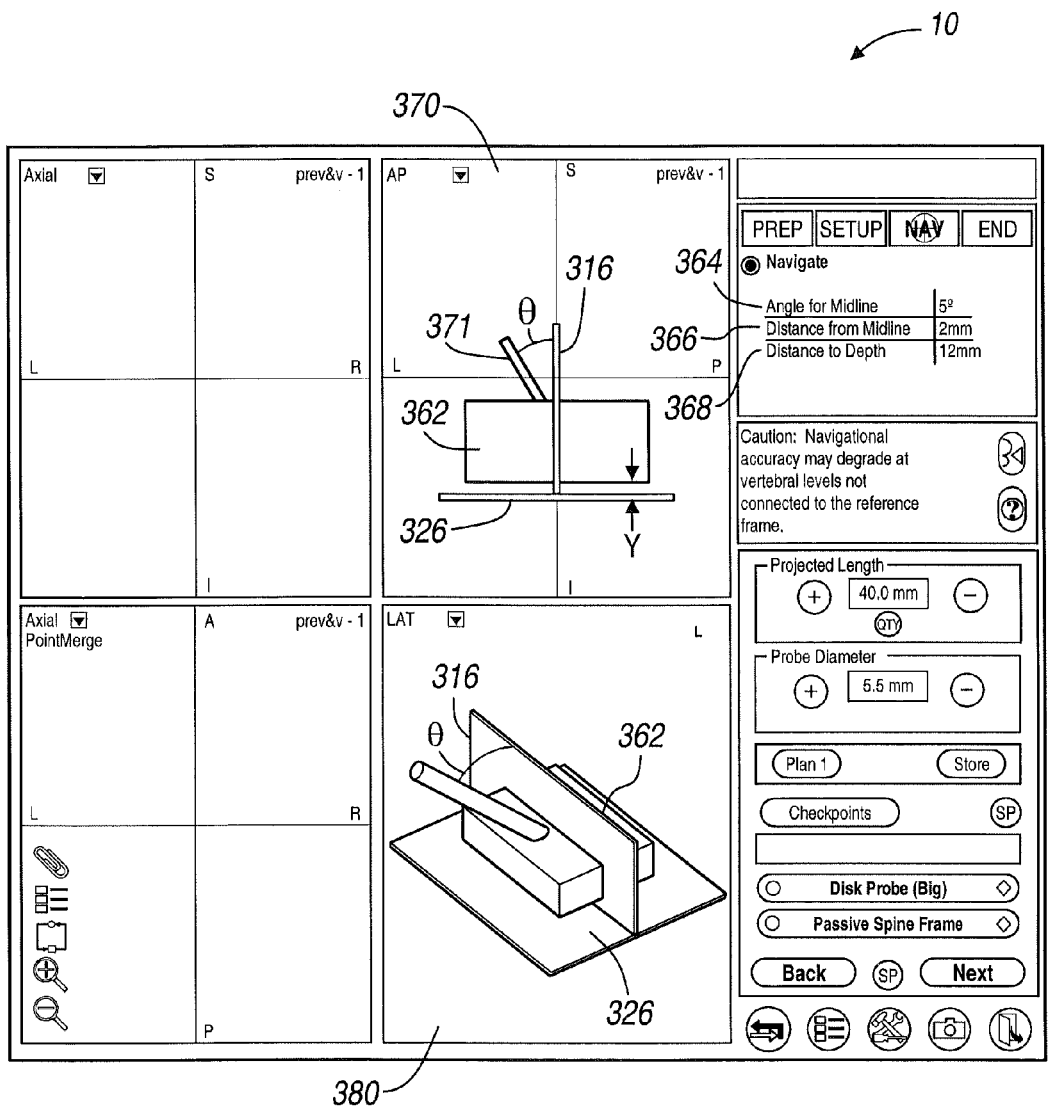
FIG. 10B is a display displaying a substantially imageless display for navigating an implant relative to the display.

With reference to FIG. 10B, the display 10 may also include a substantially imageless display. That is, the display 10 may substantially only includes an illustration of the midline plane 316 and the depth plane 326 in a two dimensional imageless view 370. The two dimensional imageless view 370 may include the respective planes 316, 326 in conjunction with the icon of the prosthesis 362 which may include $\phi$ angle as well. In addition, the graphically representation of the distance Y from the depth plane 326 may be illustrated. These substantially imageless views may also include numeral determinations of the respective variables including the angle 364 and the distance from the midline 366 and the distance from selected depth 368.

Regardless, the display 10 operable with the tracking system 44 may provide a substantially imageless display for navigating the prosthesis illustrated as the icon 362 relative to the anatomy. It will be understood, therefore, that a selection may be made depending upon the desires of the user and various other reasons to provide an image or imageless display. Regardless, after determining the various portions of the anatomy, the imageless display 370 may be used to navigate the prosthetic.

In addition, a substantially imageless three dimensional view 380 may be produced either alone or in combination with the two dimensional imageless view 370. In this case, the midline plane 316 and the depth plane 326 may be illustrated in substantially a 3-D manner with the icon 362 defining the prosthetic. As discussed above, an imageless view may be used to guide the prosthetic relative to the portions of the anatomy and displayed on the display 10. In either case, a tool portion 371 may be provided to illustrate the angle of movement relative to the midline 316 of the prosthetic icon 362.

It will be understand that a 3-D representation may be used in the display 10 that includes the images as well. Thus the navigation may be illustrated substantially 2-D or 3-D. Either may be provided for selected reasons.

Therefore, the tracking system 44 in conjunction with the system 12 may display on the display 10 a tracked position of the prosthetic such that the prosthetic icon 362 may be substantially illustrated relative to the midline 316 and the depth plane 325 during the operative procedure. In this way, the user, including a surgeon may determine the position of the prosthetic relative to the selected true midline plane 316 to substantially ensure that the prosthetic is positioned on the true midline 316 of the spine 260. As discussed above, substantially precisely positioning the implant may assist in providing a selected result and a selected anatomical orientation and range of motion after the implantation of the prosthesis. In addition, the depth plane 325 may be used to ensure that the prosthetic is positioned at a selected position relative to the spine 260, again so that a selected movement and anatomical orientation may be achieved.

Regardless, as discussed above, either an image based or an imageless system may be used. In addition, a combination or blending of the two may be used where an image based system may be used to determine the true midline 316 and the depth plane 325 or a substantially imageless system is used for tracking the procedure. Regardless, the system 12 may be used to navigate the prosthetic relative to the anatomy in block 360.

After navigating the position of the prosthetic in block 360, it may be determined to confirm the position of the prosthetic by determining whether the prosthetic is in a proper position in block 380. The confirmation of the position of the prosthetic may be performed using the imaging device 16 described above. That is, the prosthetic may include portions that are viewable with the imaging device such as radio opaque portions, tantalum balls, and the like. In addition, the prosthetic may be substantially viewable with other instruments that do not require the radio opaque portions. Regardless, the position of the implant may be confirmed either with the imaging device or the navigating system 44.

The display 10 may also display various queues to determine when the prosthetic illustrated as the icon 362 has achieved the selected depth and the position on the midline. Therefore, the icon 362 may be illustrated as a first color when the prosthetic is on the midline plane and in a selected color when the prosthetic is not on the midline plane. In addition, various visual, auditory, and central queues may be provided to illustrate that the prosthetic has been positioned in a selected position.

If the position of the prosthetic is determined to not be in a proper position or NO is chosen in block 382 and further navigation of the prosthesis may occur in block 360. Therefore, a substantially iterative process of positioning the prosthetic may occur until a YES block 384 is achieved when determining the proper position of the prosthetic. After the YES block is achieved, the patient 14 may be closed in block 386 to substantially end the operative procedure.

Therefore, the operative procedure proceeding according to method 250 may be a substantially minimally invasive procedure that is substantially navigated with the navigation system 44. The navigation system 44, including the display 10 and a workstation 36, may be used to ensure that the prosthetic is positioned relative to the spine 360, or other appropriate anatomical portion, relative to the selected anatomical definitions.

It will be understood that the workstation 36 may include portions to store the points selected by the user and the points and planes determined and defined by the system. Therefore, the system may include a storage portion, such as a hard disk, flash memory, RAM, and the like to allow for storage of the image data and the various selected and determined points and planes.

In addition, it will be understood that the images used to define the various points and lines and planes on the anatomy may be determined from substantially atlas models. That is, a stored atlas model, which may include a plurality or standardized model of a selected portion of the anatomy, may be used to determine the various points and the selected planes. The various images may then be normalized or fit to the patient 14 for a further precise position of the prosthetic. Regardless, it will be understood that images of the patient or models representing the patient may be used to select various points on the anatomy that may be used by the system to determine anatomical definitions, such as the spinal midline plane 316 and the depth plane 325.

Briefly, and also as discussed above, the method 250 may be used to perform any selected procedure. For example, a femoral implant may be positioned with the method 250. Image data of the femoral portion may be obtained and a plurality of points selected on the image data. As discussed above, the system may determine anatomical definitions therefrom. The various anatomical definitions may be used to ensure that a selected reaming and implantation of an implant, such as femoral intramedullary stem, and the like may proceed relative to a selected procedure. Therefore, the method 250 may be used to perform a procedure that does not include the spine 260 but includes any portion of the anatomy where determining anatomical definitions may assist in performing a procedure relative to the anatomical portion.

Moreover, it will be understood that the method 250 may be used to determine and navigate the prosthetic relative to a plane that is not substantially on the midline plane 316. For example, a user, or the system 12, may define a plane that is at an angle relative to the midline plane 316 for positioning the prosthetic relative to the selected anatomical portion, such as the spine 260. Therefore, the navigation in block 360 may navigate the prosthetic relative to this plane that is positioned at an angle relative to the midline 316 to achieve a selected result. Therefore, it will be understood that the system and the method 250 may be used to define any number of planes relative to the anatomical portion to allow for a selected navigation and implantation procedure of a prosthetic in the anatomy.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of selecting a position for a prosthesis to be implanted in an anatomy, comprising:
   obtaining image data of the anatomy that includes at least a portion of a spine having at least two substantially adjacent vertebrae;

displaying the obtained image data on an image device viewable by a user;

defining a plurality of points on the displayed image data corresponding at least to each of a first vertebra and a second vertebra of the at least two substantially adjacent vertebrae, the plurality of defined points including a posterior point on a spinous process, a lateral point on a transverse process, a lateral point on a vertebral body, or combinations thereof;

determining a midline of the first vertebra and the second vertebra based at least on the defined plurality of points;

determining a midline of the portion of the spine based on the determined midline of the first vertebra and the determined midline of the second vertebra;

displaying the determined spinal midline on the displayed image data relative to at least the portion of the spine;

tracking a sensor coupled to an instrument;

determining a position of the instrument relative to at least one of the defined plurality of points of the first and second vertebrae and the determined spinal midline based on tracking of the sensor;

determining an incision point relative to at least one of the defined plurality of points of the first and second vertebrae and the determined spinal midline;

navigating a surgical procedure through an incision and relative to the defined plurality of points and the determined spinal midline; and navigating the prosthesis through the incision and relative to at least the determined spinal midline to the selected position, wherein said prosthesis navigation substantially assists in positioning the prosthesis in the selected position.

2. The method of claim 1, wherein defining a plurality of defined points includes defining the plurality of points relative to the displayed image data, and storing the plurality of points relative to the image data in a storage device.

3. The method of claim 1, wherein defining a plurality of points on the displayed image data includes manipulating a user input on an image device to select certain points on the displayed image data.

4. The method of claim 1, wherein defining a plurality of points of the first and second vertebrae further includes defining lateral most points of the transverse process, defining a posterior most point of the spinous process, defining two lateral most points of the vertebral body, or combinations thereof.

5. The method of claim 1, wherein determining a midline of the portion of the spine further includes:
    determining an orientation of the obtained image data; and
    displaying the determined spinal midline obliquely relative to the obtained image data.

6. The method of claim 1, wherein the determined spinal midline includes a substantially weight bearing spinal midline.

7. The method of claim 1, further comprising displaying a representative position of the prosthesis relative to at least one of the defined plurality of points, the determined midlines of the first and second vertebrae, or the determined spinal midline.

8. The method of claim 7, further comprising displaying cues for a user to assist in positioning the prosthesis.

9. The method of claim 8, wherein the cues include icons, the icons arranged to change based on the representative position of the prosthesis moving closer to the determined spinal midline.

10. The method of claim 7, further comprising tracking a position of the prosthesis with a sensor coupled to the prosthesis.

11. The method of claim 7, further comprising:
    implanting the prosthesis selected from the group including a disc, a nucleous, a fusion apparatus, a bladder implant, or combinations thereof between the first and second vertebrae; and
    verifying a position of the implanted prosthesis corresponds to the selected position of the prosthesis.

12. The method of claim 1, further comprising:
    removably coupling the instrument to the prosthesis;
    tracking a position of the prosthesis with the sensor; and
    displaying a representative position of the prosthesis relative to the displayed image data and the displayed spinal midline;
    wherein navigating the prosthesis includes navigating the prosthesis with the instrument.

13. The method of claim 1, wherein the prosthesis is an expandable prosthesis and includes at least one trackable sensor, the prosthesis being positioned relative to at least the determined spinal midline and the defined plurality of points, and wherein expansion of the expandable prosthesis is tracked via the trackable sensor.

14. The method of claim 13, wherein the expandable prosthesis includes a bladder implant.

15. A method of selecting a position for a prosthesis to be implanted in an anatomy, comprising:
    obtaining image data of the anatomy that includes at least a portion of a spine having at least two substantially adjacent vertebrae, and displaying the obtained image data to be viewable by a user;
    positioning a dynamic reference frame relative to at least one of a first vertebra or a second vertebra of the two substantially adjacent vertebrae such that the dynamic reference frame is moveable with the at least one of the first and second vertebrae;
    defining a plurality of points on the displayed image data corresponding at least to each of the first and second vertebrae;
    determining a midline of the first vertebra and the second vertebra on the displayed image data based at least on the defined plurality of points;
    determining a midline of the portion of the spine on the displayed image data based at least on the determined midlines of the first and second vertebrae;
    tracking a sensor coupled to an instrument;
    determining a position of the instrument relative to at least one of the defined plurality of points of the first and second vertebrae and the determined spinal midline based on tracking of the sensor;
    navigating a surgical procedure relative to the defined plurality of points and the determined spinal midline, including manipulating a position of at least one of the first or second vertebrae;
    positioning a prosthesis template relative to the first and second vertebrae and displaying an image of the template relative to the first and second vertebrae on the displayed image data; and
    updating the displayed image data using at least the dynamic reference frame to reflect the manipulated position of the at least one of the first or second vertebrae relative to the instrument and the determined spinal midline.

16. The method of claim 15, further comprising using the template to select an appropriate prosthesis and to determine an appropriate amount of resection.

17. The method of claim 16, further comprising using the template for determining a selected position for the prosthesis based in part on the displayed image data of the template relative to the first and second vertebrae.

18. The method of claim 15, further comprising:
providing the prosthesis with a sensor arrangement such that a real-time position of the prosthesis can be tracked and displayed relative to the obtained image data of the anatomy and the determined spinal midline to assist in navigating the prosthesis to the selected position;
implanting the prosthesis selected from the group including a disc, a nucleus, a fusion apparatus, a bladder implant, or combinations thereof between the first and second vertebrae; and
verifying an implanted position of the prosthesis corresponds to the selected position of the prosthesis.

19. The method of claim 18, wherein the sensor arrangement is removably connected to the prosthesis, and wherein the sensor arrangement is removed after implantation and verification of the implanted position of the prosthesis.

20. The method of claim 15, wherein the dynamic reference frame is operable in connection with a processor to generate an alert based on movement of the dynamic reference frame relative to a previously known or selected location.

21. The method of claim 15, wherein the dynamic reference frame includes a first dynamic reference frame associated with the first vertebra and a second dynamic reference frame associated with the second vertebra, and
wherein the first and second dynamic reference frames are operable in connection with a processor to update and display any real-time movement of the respective first and second vertebrae relative to at least the obtained image data and the defined plurality of points on the displayed image data.

22. The method of claim 21, wherein manipulating a position of at least one of the first and second vertebrae includes distracting the first and second vertebrae to a distracted position to assist in a resection of the spine, and
wherein the first and second dynamic reference frames are operable in connection with a processor and an image device to update and display the distracted position of the first and second vertebrae relative to each other, the obtained image data, the instrument and the determined spinal midline.

23. The method of claim 15, further comprising displaying navigational information of the surgical procedure relative to the obtained image data of the anatomy;
wherein the navigational information includes displaying at least one of a distance from a selected plane, an angle relative to a selected plane, a distance to a selected plane or point, and combinations thereof.

24. The method of claim 15, wherein defining a plurality of points includes defining the plurality of points relative to the displayed image data, and storing the defined plurality of points relative to the image data in a storage device.

25. The method of claim 15, wherein defining a plurality of points on the displayed image data includes manipulating a user input on an image device to select certain points on the displayed image data.

26. The method of claim 15, wherein determining a midline of the portion of the spine further includes:
determining an orientation of the obtained image data; and
displaying the determined spinal midline obliquely relative to the obtained image data.

27. The method of claim 15, wherein the determined spinal midline includes a substantially weight bearing spinal midline.

28. A method of selecting a position for a prosthesis to be implanted in an anatomy, comprising:
obtaining image data of the anatomy that includes at least a portion of a spine having at least two substantially adjacent vertebrae, and displaying the obtained image data to be viewable by a user;
positioning a first dynamic reference frame relative to a first vertebra of the substantially two adjacent vertebrae and a second dynamic reference frame relative to a second vertebra of the substantially two adjacent vertebra such that such that the first and second dynamic reference frames are each moveable with the respective first and second vertebrae;
defining a plurality of points on the displayed image corresponding at least to each of the first or second vertebrae;
determining a midline of the first vertebra and the second vertebra on the displayed image data based at least on the defined plurality of points;
determining a midline of the portion of the spine on the displayed image data based at least on the determined midlines of the first and second vertebrae;
navigating a surgical procedure relative to the defined plurality of points and the determined spinal midline, including distracting the first and second vertebrae to a distracted position;
updating the displayed image data using at least the first and second dynamic reference frames to reflect the distracted position of the first and second vertebrae relative to the determined spinal midline and the defined plurality of points;
tracking a sensor associated with the prosthesis; and
positioning the prosthesis relative to the distracted first and second vertebrae.

29. The method of claim 28, further comprising determining a depth plane relative to the determined spinal midline and based on the obtained image data and the defined plurality of points.

30. The method of claim 29, further comprising positioning the prosthesis relative to the determined spinal midline and the depth plane, and wherein the sensor is coupled to the prosthesis.

31. The method of claim 29, further comprising:
coupling an instrument to the prosthesis, the instrument including the sensor;
tracking the prosthesis via the sensor relative to the determined spinal midline, the defined plurality of points, the depth plane, or combinations thereof; and
positioning the prosthesis relative to the determined spinal midline and depth plane.

32. A method of selecting a position for a prosthesis to be implanted in an anatomy, comprising:
obtaining image data of the anatomy that includes at least a portion of a spine having at least two substantially adjacent vertebrae;
displaying the obtained image data on an image device viewable by a user;
defining a plurality of points on the displayed image data corresponding at least to each of a first vertebra and a second vertebra of the at least two substantially adjacent vertebrae, the plurality of defined points including a posterior point on a spinous process, a lateral point on a transverse process, a lateral point on a vertebral body, or combinations thereof;

determining a midline of the first vertebra and the second vertebra based at least on the defined plurality of points;

determining a midline of the portion of the spine based on the determined midline of the first vertebra and the determined midline of the second vertebra;

displaying the determined spinal midline on the displayed image data relative to at least the portion of the spine; and navigating the prosthesis relative to at least the determined spinal midline to the selected position, wherein said prosthesis navigation substantially assists in positioning the prosthesis in the selected position.

33. A method of selecting a position for a prosthesis to be implanted in an anatomy, comprising:

obtaining image data of the anatomy that includes at least a portion of a spine having at least two substantially adjacent vertebrae, and displaying the obtained image data to be viewable by a user;

positioning a dynamic reference frame relative to at least one of a first vertebra or a second vertebra of the two substantially adjacent vertebrae such that the dynamic reference frame is moveable with the at least one of the first and second vertebrae;

defining a plurality of points on the displayed image data corresponding at least to each of the first and second vertebrae;

determining a midline of the first vertebra and the second vertebra on the displayed image data based at least on the defined plurality of points;

determining a midline of the portion of the spine on the displayed image data based at least on the determined midlines of the first and second vertebrae;

navigating the prosthesis relative to the defined plurality of points and the determined spinal midline, including manipulating a position of at least one of the first or second vertebrae; and updating the displayed image data using at least the dynamic reference frame to reflect the manipulated position of the at least one of the first or second vertebrae relative to the determined spinal midline.

* * * * *